United States Patent
Pimentel et al.

(10) Patent No.: US 9,851,361 B2
(45) Date of Patent: Dec. 26, 2017

(54) METHODS OF COMPARING ANTI-VINCULIN AND ANTI-CYTOLETHAL DISTENDING TOXIN ANTIBODIES AS THEY RELATE TO IRRITABLE BOWEL SYNDROME

(71) Applicant: Cedars-Sinai Medical Center, Los Angeles, CA (US)

(72) Inventors: Mark Pimentel, Los Angeles, CA (US); Christopher Chang, Los Angeles, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 0 days.

(21) Appl. No.: 15/021,850

(22) PCT Filed: Oct. 9, 2014

(86) PCT No.: PCT/US2014/059957
§ 371 (c)(1),
(2) Date: Mar. 14, 2016

(87) PCT Pub. No.: WO2015/054529
PCT Pub. Date: Apr. 16, 2015

(65) Prior Publication Data
US 2017/0038393 A1    Feb. 9, 2017

Related U.S. Application Data

(60) Provisional application No. 61/888,658, filed on Oct. 9, 2013.

(51) Int. Cl.
*G01N 33/68* (2006.01)

(52) U.S. Cl.
CPC ..... *G01N 33/6854* (2013.01); *G01N 33/6893* (2013.01); *G01N 2800/065* (2013.01)

(58) Field of Classification Search
CPC ........... G01N 33/6854; G01N 33/6893; G01N 2800/065
See application file for complete search history.

(56) References Cited

U.S. PATENT DOCUMENTS

| | | |
|---|---|---|
| 6,805,852 B2 | 10/2004 | Lin et al. |
| 6,861,053 B1 | 3/2005 | Lin et al. |
| 7,048,906 B2 | 5/2006 | Lin et al. |
| 7,056,686 B2 | 6/2006 | Lin et al. |
| 7,081,239 B2 | 7/2006 | Lin |
| 7,244,412 B2 | 7/2007 | Lin |
| 7,452,857 B2 | 11/2008 | Lin et al. |
| 7,585,838 B2 | 9/2009 | Lin et al. |
| 7,605,240 B2 | 10/2009 | Lin et al. |
| 7,608,245 B2 | 10/2009 | Lin |
| 7,615,207 B2 | 11/2009 | Lin |
| 7,718,608 B2 | 5/2010 | Lin et al. |
| 7,736,622 B2 | 6/2010 | Lin et al. |
| 7,935,799 B2 | 5/2011 | Lin et al. |
| 8,110,177 B2 | 2/2012 | Lin et al. |
| 8,197,805 B2 | 6/2012 | Lin et al. |
| 8,388,935 B2 | 3/2013 | Lin et al. |
| 8,562,952 B2 | 10/2013 | Lin et al. |
| 9,110,081 B2 | 8/2015 | Pimentel et al. |
| 9,358,276 B2 | 6/2016 | Lin et al. |
| 2004/0018528 A1 | 1/2004 | Morimoto et al. |
| 2006/0127359 A1 | 6/2006 | Borrelli |
| 2006/0193871 A1 | 8/2006 | Lin |
| 2007/0212691 A1 | 9/2007 | Yamasaki et al. |
| 2011/0183337 A1 | 7/2011 | Von Stein et al. |
| 2011/0294726 A1 | 12/2011 | Pimentel et al. |
| 2011/0305704 A1 | 12/2011 | Pimentel et al. |
| 2012/0088257 A1 | 4/2012 | Mouthon et al. |
| 2014/0206636 A1 | 7/2014 | Lin et al. |
| 2015/0233944 A1 | 8/2015 | Pimentel et al. |
| 2016/0061837 A1 | 3/2016 | Pimentel et al. |
| 2016/0103136 A1 | 4/2016 | Pimentel et al. |
| 2017/0095543 A1 | 4/2017 | Lin et al. |

FOREIGN PATENT DOCUMENTS

| | | |
|---|---|---|
| AU | 2002256254 B2 | 5/2007 |
| AU | 2007201246 A1 | 3/2009 |
| AU | 2010213708 B2 | 12/2015 |
| AU | 2014331841 A1 | 3/2016 |
| AU | 2015330872 A1 | 4/2017 |
| BR | 112016007474-2 A2 | 9/2017 |
| CA | 2923651 A1 | 4/2015 |
| CA | 2962493 A1 | 4/2016 |
| CA | 2444548 C | 6/2016 |
| CL | 2011-1944 | 2/2012 |
| CL | 2016000820 A1 | 9/2016 |
| CN | 105744956 A1 | 7/2016 |

(Continued)

OTHER PUBLICATIONS

PCT/US2010/023911 International Search Report and Written Opinion dated May 14, 2010; 11 pages.
PCT/US2010/023911 International Preliminary Report on Patentability dated Aug. 16, 2011; 8 pages.
PCT/US2013/005626 International Search Report and Written Opinion dated Aug. 18, 2014; 14 pages.
PCT/US2013/005626 International Preliminary Report on Patentability dated Aug. 18, 2014; 12 pages.
PCT/US2014/059957 International Search Report and Written Opinion dated Jan. 8, 2015; 11 pages.
PCT/US2014/059957 International Preliminary Report on Patentability dated Apr. 21, 2016; 9 pages.
PCT/US2015/054655 International Search Report and Written Opinion dated Feb. 12, 2016; 7 pages.

(Continued)

*Primary Examiner* — Robert S Landsman
(74) *Attorney, Agent, or Firm* — Linda B. Huber; Nixon Peabody LLP

(57) ABSTRACT

The present invention describes methods, assays, and systems of diagnosing, selecting and treating irritable bowel syndrome (IBS) based on a subject's level of anti-vinculin and anti-CdtB antibodies. IBS can be distinguished from inflammatory bowel (IBD) disease using the methods, assays, and systems described herein.

20 Claims, 2 Drawing Sheets

(56) References Cited

FOREIGN PATENT DOCUMENTS

| | | |
|---|---|---|
| CN | 107003308 A | 8/2017 |
| CO | 16091069 | 9/2016 |
| EP | 1 385 476 | 2/2004 |
| EP | 2 261 665 B1 | 6/2004 |
| EP | 1 200 828 B1 | 10/2007 |
| EP | 2 261 664 A2 | 12/2010 |
| EP | 2 305 213 A2 | 4/2011 |
| EP | 1 811 303 B1 | 6/2011 |
| EP | 2 370 435 B1 | 1/2015 |
| EP | 2 256 498 B1 | 4/2015 |
| EP | 2 895 856 | 7/2015 |
| EP | 2 267 445 B1 | 8/2016 |
| EP | 3054977 A1 | 8/2016 |
| EP | 3204771 A1 | 8/2017 |
| HK | 1221898 A1 | 6/2017 |
| JP | 2009-102401 | 5/2009 |
| JP | 4653936 | 12/2010 |
| JP | 2017502253 A | 1/2017 |
| KR | 20160062161 A | 6/2016 |
| KR | 20170067795 A | 6/2017 |
| MX | 2016004167 A | 6/2016 |
| PE | 08822016 A1 | 9/2016 |
| SG | 11201601733V A | 4/2016 |
| SG | 11201702395W A | 4/2017 |
| WO | WO 01/11077 A2 | 2/2001 |
| WO | WO 01/11334 A2 | 2/2001 |
| WO | WO 2002/083926 A2 | 10/2002 |
| WO | WO 2004/024097 A2 | 3/2004 |
| WO | WO 2010/093801 A1 | 8/2010 |
| WO | WO 2012/007913 A2 | 1/2012 |
| WO | WO 2014/042828 A2 | 3/2014 |
| WO | WO 2015/054529 A1 | 4/2015 |
| WO | WO 2016/057772 A1 | 4/2016 |

OTHER PUBLICATIONS

EP Application No. 10741728.9 Extended Search Report dated Oct. 17, 2014; 7 pages.

EP Application No. 13837424.4 Extended Search Report dated May 9, 2016; 8 pages.

Abuoun et al. Cytolethal Distending Toxin (CDT)—Negative Campylobacter jejuni Strains and Anti-CDT Neutralizing Antibodies are Induced during Human Infection but Not during Colonization in Chickens. Infection and Immunity (2005). 73(5): 3053-3062.

Air et al. Mechanism of Antigenic Variation in an Individual Epitope on Influenza Virus N9 Neuraminidase. Journal of Virology (1990). 64(12):5797-5803.

Bourke, B. Campylobacter infection: small bowel and colon. Current Opinion in Gastroenterology. (2002). 18:4-9.

Cambridge et al. Anti-neutrophil antibodies in inflammatory bowel disease: prevalence and diagnostic role. Gut (2013). 33:668-674.

Carey et al. A prospective evaluation of the pathogenesis of detrusor instability in woman, using electron microscopy and immunohistochemistry. BJU International (2000). 86:970-976.

Colman, PM. Effects of amino acid sequence changes on antibody-antigen interactions. Res Immunol (1994). 145(1):33-6.

Dunlop et al. Relative Importance of Enterochromaffin Cell Hyperplasia, Anxiety, and Depression in Postinfective IBS. Gastroenterology (2003). 125:1651-1659.

Fox et al. Gastroenteritis in NF-kappaB-deficient mice is produced with wildtype Camplyobacter jejuni but not with C. jejuni lacking cytolethal distending toxin despite persistent colonization with both strains. Infection & Immunity (2004). 72(2):1116-25.

Hickey et al. Campylobacter jejuni Cytolethal Distending Toxin Mediates Release of Interleukin-8 from Intestinal Epithelial Cells. Infection and Immunity (2000). 68(12):6535-6541.

Mariuzza et al. The structural basis of antigen-antibody recognition. Annu Rev Biophys Biophys Chem (1987). 16:139-59. Abstract Only.

Morales et al. Antibodies to an 18-Residue Peptide of Cdt Are Found in the Serum of Rats in a Model of Post-Infectious IBS. Gastroenterology (2011). 140(5), p. S-371.

Morales et al. Antibodies to Cytolethal Distending Toxin of Campylobacter Jejuni Bind to Enteric Neuronal Elements: Further Evidence for Molecular Mimicry. Gastroenterology (2012). 142(5): Suppl 1.

Morales et al. Tu2056 Antibodies to Cytolethal Distending Toxin B and Auto-Antibodies to Human Vinculin are Elevated in IBS Subjects. Gastroenterology (2013). 144(5): Suppl. 1, p. S-914.

Morales et al. Effect of Rifaximin Treatment on Anti-Vinculin Antibodies in IBS with Diarrhea. Gastroenterology (2016).150(4). Supplement 1. p. S-695.

Moss-Morris et al. To "Lump" or to "Split" the Functional Somatic Syndromes: Can Infections and Emotional Risk Factors Differentiate between the Onset of Chronic Fatigue Syndrome and Irritable Bowel Syndrome. Psychosomatic Medicine (2006). 68:463-469.

Neal et al. Prevalence of Gastrointestinal Symptoms Six Months after Bacterial Gastroenteritis and Risk Factors for Development of the Irritable Bowel Syndrome: Postal Survey of Patients. BMJ (1997). 314:779, 14 pages.

Nelson et al. Vinculin Activators Target Integrins from within the Cell to Increase Melanoma Sensitivity to Chemotherapy. Molecular Cancer Research (2011). 9(6):1-12.

Nemeth et al. Altered Cytoskeleton in Smooth Muscle of Aganglionic Bowel. Arch Pathol Lab Med (2002). 126:692-696.

Novak, K. A Serologic Test for Irritable Bowel Syndrome and Other News from ACG. Gastroenterology Press Highlights (2013); pp. 1-2. Retrieved from: <www.gastrojournal.org/pb/assets/raw/Health%20Advance/journals/ygast/November26_PressHighlight3.pdf on Feb 3, 2016.

Peng et al. a-Catenin Uses a Novel Mechanism to Activate Vinculin. The Journal of Biological Chemistry (2012). 287(10): 7728-7737.

Pimentel et al. A New Rat Model Links Two Complementary Theories in Irritable Bowel Syndrome. Digestive Diseases and Sciences (2007). 53(4):982-989.

Pimentel et al. Development and Validation of a Biomarker for Diarrhea-Predominant Irritable Bowel Syndrome in Human Subjects. PLoS One (2015). 10(5): pp. 1-12.

Purdy et a. Characterisation of cytolethal distending toxin (CDT) mutants of Campylobacter jejuni. J. Med. Microbiol. (2000). 49: pp. 473-479.

Rezaie et al. Assessment of Anti-Vinculin and Anti-CdtB Antibodies in IBS Subtypes. Gastroenterology (2016).150(4). Supplement 1. p. S62.

Rolle et al. Structural basis of voiding dysfunction in megacystis microcolon intestinal hypoperistalsis syndrome. Journal of Pediatric Urology (2006). 2:277-284.

Spiller et al. Increased rectal mucosal enteroendocrine cells, T lymphocytes, and increased gut permeability following acute Campylobacter enteritis and inpost-dysenteric irritable bowel syndrome. Gut (2000). 47:804-811.

Suh et al. Patients with irritable bowel syndrome or constipation have an increased risk for ischaemic colitis. Alimentary Pharmacology & Therapeutics (2007). 25:681-692.

Sung et al. Antibody to Cytolethal Distending Toxin of Campylobacter Jejuni Stains Small Bowel Myenteric Neuromuscular Elements in Control and C. Jejuni Exposed Rats: A Possible Role of Molecular Mimicry. Gastroenterology (2010). 138(5). p. S-770.

Trees et al. Genome Sequences of 228 Shiga Toxin-Producing *Escherichia coli* Isolates and 12 Isolates Representing Other Diarrheagenic *E. coli* Pathotypes. Genome Announc (2014). 2(4): 3 pages.

Turkay et al. Noninvasive Methods in Evaluation of Inflammatory Bowel Disease: Where Do We Stand Now? An Update. Clinics (2010). 65(2):221-31.

EP Application No. 148516883 Extended Search Report dated Mar. 10, 2017; 10 pages.

Lembo et al. Use of serum biomarkers in a diagnostic test for irritable bowel syndrome. Alimentary Pharmacology & Therapeutics (2009). 29:834-842.

Pimentel et al. Anti-vinculin antibodies: Multicenter validation of a diagnostic blood test for irritable bowel syndrome. The American Journal of Gastroenterology (2013). 108:1887; p. S571. Abstract Only.

(56) References Cited

OTHER PUBLICATIONS

Pimentel et al. Autoimmunity to vinculin in humans may be important in the pathophysiology of IBS. Gastroenterology (2014). 146(5); suppl 1, Su2020. Abstract Only.

Triantafyllou et al. Evaluating the Role of Cytolethal Distending Toxin in the Development of Small Intestinal Bacterial Overgrowth in a Rat Model Post-Infectious IBS. Gastroenterology (2014). 146(5): suppl 1, Su1424. Abstract Only.

Singapore Application No. 11201601733V Written Opinion dated Apr. 17, 2017; 8 pages.

METHODS OF COMPARING ANTI-VINCULIN AND ANTI-CYTOLETHAL DISTENDING TOXIN ANTIBODIES AS THEY RELATE TO IRRITABLE BOWEL SYNDROME

CROSS-REFERENCE TO RELATED APPLICATIONS

This application is a National Phase of International Application No. PCT/US2014/059957, filed Oct. 9, 2014, which designated the U.S. and that International Application was published under PCT Article 21(2) in English, which also includes a claim of priority under 35 U.S.C. §119(e) to U.S. provisional patent application No. 61/888,658, filed Oct. 9, 2013, the entirety of which is hereby incorporated by reference.

FIELD OF INVENTION

This invention relates to the diagnosis and treatment of irritable bowel syndrome.

BACKGROUND

The following description includes information that may be useful in understanding the present invention. It is not an admission that any of the information provided herein is prior art or relevant to the presently claimed invention, or that any publication specifically or implicitly referenced is prior art.

The diagnosis of irritable bowel syndrome (IBS) has been a diagnosis of exclusion or a diagnosis based on a patient's presenting symptoms. Further, when patients present with gastrointestinal symptoms, distinguishing irritable bowel syndrome (IBS) from other types of gastrointestinal ailments, such as inflammatory bowel disease (IBD) (e.g., ulcerative colitis, Crohn's disease), can be difficult or can require invasive procedures to rule out IBD. Currently in the art, there is no means of diagnosing IBS or distinguishing IBS from other disorders of bowel dysfunction. The convention usually requires invasive testing which has inherent risks, great expense and morbidity to patients.

Accordingly, there remains a need in the art for methods and systems to diagnose IBS and to distinguish between IBS and IBD, particularly in less invasive fashions.

SUMMARY OF THE INVENTION

The following embodiments and aspects thereof are described and illustrated in conjunction with compositions and methods which are meant to be exemplary and illustrative, not limiting in scope.

Various embodiments provide for a method of diagnosing IBS, and optionally selecting a treatment for IBS or optionally administering an IBS therapy, comprising providing a biological sample from a subject desiring a diagnosis regarding IBS; assaying the biological sample for a level of anti-vinculin antibodies and a level of anti-CDT antibodies; determining the difference between the level of anti-vinculin antibodies and the level of anti-CDT antibodies; and determining the presence of IBS when the level of anti-vinculin antibodies is higher than the level of anti-CDT antibodies.

Various embodiments provide for a method of distinguishing between IBS and IBD, and optionally selecting a treatment for IBS or optionally administering an IBS therapy, comprising: providing a biological sample from a subject desiring a diagnosis to distinguish between IBS and IBD; assaying the biological sample for a level of anti-vinculin antibodies and a level of anti-CDT antibodies; and determining the presence of IBS when the level of anti-vinculin antibodies is higher than the level of anti-CDT antibodies, or determining the difference between the level of anti-vinculin antibodies and the level of anti-CDT antibodies.

In various embodiments, assaying the biological sample can comprise: contacting vinculin or a fragment thereof to the biological sample; contacting CdtB or a fragment thereof to the biological sample, wherein anti-vinculin and/or anti-CdtB antibodies specifically bind to the vinculin or the fragment thereof and/or the CdtB or the fragment thereof in the biological sample; and measuring the levels of the anti-vinculin antibodies and the anti-CdtB antibodies in the biological sample.

In various embodiments, the subject can be determined to have IBS if the level of anti-vinculin antibodies is 25% or more higher than the level of anti-CDT antibodies.

In various embodiments, optical density (OD) can be used to measure the level of anti-vinculin antibodies and anti-CDT antibodies, and when the difference between the OD of anti-vinculin antibodies ($OD_V$) and OD of anti-CDT antibodies ($OD_{CDT}$) is greater than 0, the subject can be determined to have IBS.

In various embodiments, when $OD_V - OD_{CDT}$ is greater than 0.2, the subject can be determined to have IBS.

In various embodiments, the anti-vinculin antibody can be an antibody that binds specifically to vinculin. In various embodiments, the anti-vinculin antibody can be an antibody that binds specifically to a 5, 6, 7, 8, 9, 10, 11, 12, 13, 14, 15, 16, 17, 18, 19, 20, 21, or 22 residue peptide that has at least 95%, 96%, 97%, 98%, 99% or 100% homology with 5, 6, 7, 8, 9, 10, 11, 12, 13, 14, 15, 16, 17, 18, 19, 20, 21, or 22 contiguous residues of vinculin or SEQ ID NO.:7.

In various embodiments, the anti-vinculin antibody can be an antibody that binds specifically to a polypeptide comprising 5, 6, 7, 8, 9, 10, 11, 12, 13, 14, 15, 16, 17, 18, 19, 20, 21, or 22 residues that has at least 95%, 96%, 97%, 98%, 99% or 100% homology with 5, 6, 7, 8, 9, 10, 11, 12, 13, 14, 15, 16, 17, 18, 19, 20, 21, or 22 contiguous residues of vinculin or SEQ ID NO:7.

In various embodiments, the anti-CDT antibody can be an antibody that binds specifically to the CdtB subunit of CDT.

In various embodiments, the CdtB amino acid sequence can be *Campylobacter jejuni* cytolethal distending toxin B (SEQ ID NO: 5).

In various embodiments, the anti-CDT antibody can be an antibody that binds specifically to an amino acid sequence at least 80%, 85%, 90%, 95%, 96%, 97%, 98%, or 99% identical to SEQ ID NO: 5.

The method of claim 10, wherein the CdtB amino acid sequence is *Campylobacter coli* cytolethal distending toxin B (SEQ ID NO: 1). In various embodiments, the anti-CDT antibody can be an antibody that binds specifically to an amino acid sequence at least 80%, 85%, 90%, 95%, 96%, 97%, 98%, or 99% identical to SEQ ID NO: 1.

In various embodiments, the anti-CDT antibody can be an antibody that binds specifically to a polypeptide comprising 5, 6, 7, 8, 9, 10, 11, 12, 13, 14, 15, 16, 17, 18, 19, 20, 21, or 22 residues that has at least 80%, 85%, 90%, 95%, 96%, 97%, 98%, 99% or 100% homology with 5, 6, 7, 8, 9, 10, 11, 12, 13, 14, 15, 16, 17, 18, 19, 20, 21, or 22 contiguous residues of CdtB.

In various embodiments, the method can further comprise selecting an IBS treatment for the subject if the subject is determined to have IBS.

In various embodiments, the method can further comprise administering an IBS therapy to the subject if the subject is determined to have IBS.

Various embodiments provide for a system to diagnose IBS comprising: an isolated biological sample from a subject desiring a diagnosis regarding IBS; and one or more assays for detecting a level of anti-vinculin antibodies and a level of anti-CDT antibodies to diagnose IBS.

Various embodiments provide for a system to distinguish between IBS and IBD, comprising: an isolated biological sample from a subject desiring a diagnosis to distinguish between IBS and IBD; and one or more assays to detect a level of anti-vinculin antibodies and a level of anti-CDT antibodies to distinguish between IBS and IBD.

In various embodiments, the system can further comprise a machine for determining a presence of IBS when the level of anti-vinculin antibodies is higher than the level of anti-CDT antibodies.

In various embodiments, the system can further comprise an output or display element for displaying whether the patient has IBS, and/or for displaying whether the anti-vinculin antibodies is higher than the level of anti-CDT antibodies.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

DESCRIPTION OF THE INVENTION

Figure 1:
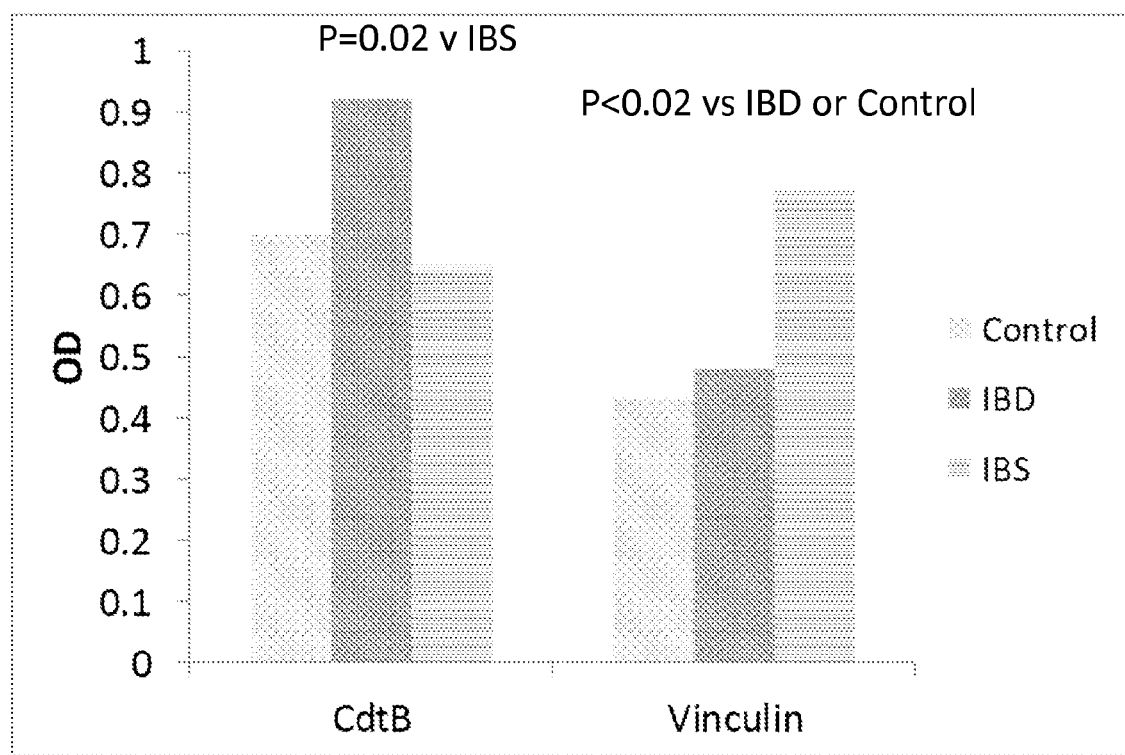
FIG. 1 depicts the optical density of anti-vinculin antibodies ($OD_V$) and the optical density of anti-CDTB antibodies ($OD_{CDTB}$) in accordance with various embodiments of the present invention.
Figure 2:
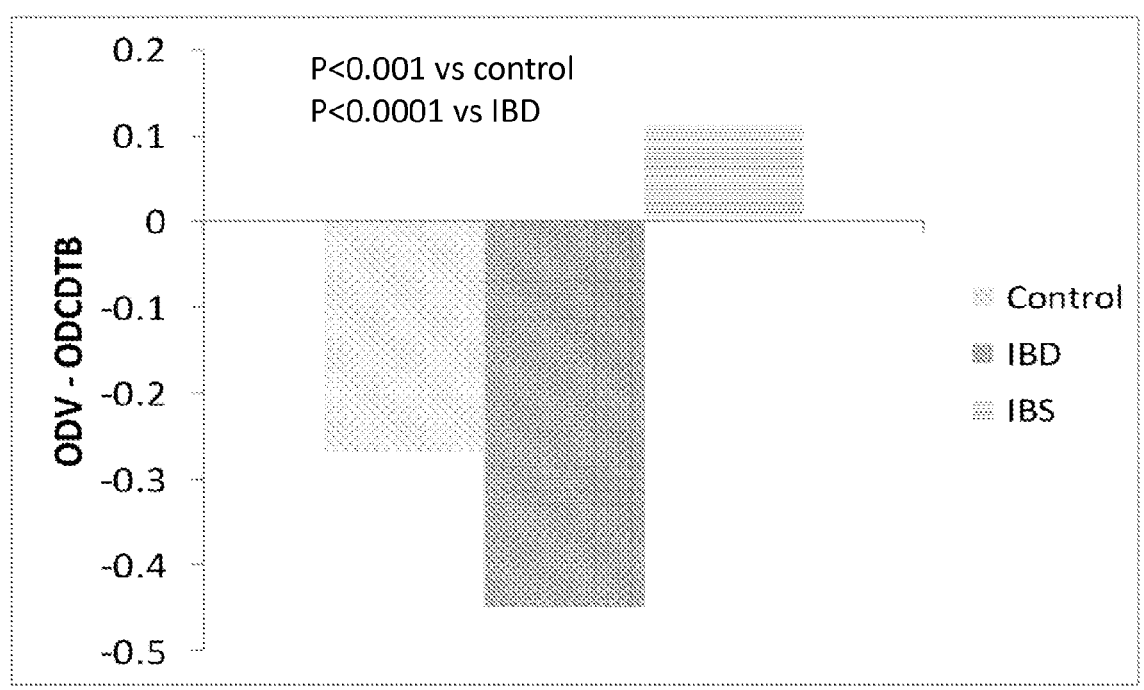
FIG. 2 depicts the difference between the optical density of anti-vinculin antibodies ($OD_V$) and the optical density of anti-CDTB antibodies ($OD_{CDTB}$) in accordance with various embodiments of the present invention.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., Revised, J. Wiley & Sons (New York, N.Y. 2006); and Sambrook and Russel, *Molecular Cloning: A Laboratory Manual* 4$^{th}$ ed., Cold Spring Harbor Laboratory Press (Cold Spring Harbor, N.Y. 2012), provide one skilled in the art with a general guide to many of the terms used in the present application. For references on how to prepare antibodies, see D. Lane, *Antibodies: A Laboratory Manual* 2$^{nd}$ ed. (Cold Spring Harbor Press, Cold Spring Harbor N.Y., 2013); Kohler and Milstein, (1976) Eur. J. Immunol. 6: 511; Queen et al. U.S. Pat. No. 5,585,089; and Riechmann et al., Nature 332: 323 (1988); U.S. Pat. No. 4,946,778; Bird, Science 242:423-42 (1988); Huston et al., Proc. Natl. Acad. Sci. USA 85:5879-5883 (1988); Ward et al., Nature 334: 544-54 (1989); Tomlinson I. and Holliger P. (2000) Methods Enzymol, 326, 461-479; Holliger P. (2005) Nat. Biotechnol. September; 23(9):1126-36).

One skilled in the art will recognize many methods and materials similar or equivalent to those described herein, which could be used in the practice of the present invention. Indeed, the present invention is in no way limited to the methods and materials described.

"Antibody" or "antibodies" as used herein include polyclonal antibodies, monoclonal antibodies, antibody variants such as single chain (recombinant) Fv, human antibodies, humanized antibodies, chimeric antibodies, and immunologically active fragments of antibodies.

"Binds specifically" as used herein refers to the act of an antibody binding to its antigen and is intended to exclude low-level, non-specific binding that may occur between random proteins. "Binds specifically" as used herein is not intended and does not imply that the antibody will not bind to any protein other than the proteins or polypeptides as disclosed herein since antibodies can cross-react with any protein that includes the relevant epitope.

"Severe irritable bowel syndrome" as used herein refers to irritable bowel syndrome (IBS) in a subject who is referred to or would have been referred to a tertiary care center, an IBS specialist, or a motility specialist.

The inventors have determined that CdtB appeared not to simply be acting through direct toxicity but rather through the cross-reaction of antibodies to CdtB with the host protein, vinculin. Vinculin is a 117-kDa cytoplasmic actin-binding protein that is a key component of both focal adhesions and aherens junctions, mediating the link between integrins or cadherins respectively and the actin cytoskeleton.

Based on these pathophysiologic observations in an animal model, the inventors believe that exposure to CdtB led to autoimmunity to vinculin based on molecular mimicry. Described herein, the effectiveness of detecting these events as a test for IBS in humans are evaluated.

The study herein shows that when anti-vinculin antibodies are greater than anti-CdtB antibodies it is highly indicative IBS and distinguishes IBS from IBD. While not wishing to be bound to any particular theory, the inventors believe that when anti-vinculin antibodies are greater than anti-CdtB antibodies it is also indicative of the severity of the IBS experienced by the patients. The IBS patients in the study described herein were seen at tertiary care centers, which strongly imply the severity of the condition. Patients typically are not referred to or seek treatment at tertiary care centers unless their conditions are severe. They typically will self-treat or treat with their primary care physicians. Further, these patients are highly likely to have been refractory to some IBS therapies, which usually warrant a referral to a tertiary care center.

Diagnosis

Various embodiments of the present invention provide for methods, assays, and systems of diagnosing IBS and distinguishing between IBS and IBD.

Methods

Various embodiments of the present invention provide for a method of diagnosing IBS comprising: providing a biological sample from a subject desiring a diagnosis regarding IBS; assaying the biological sample for a level of anti-vinculin antibodies and a level of anti-CDT antibodies; determining the difference between the level of anti-vinculin antibodies and the level of anti-CDT antibodies, and determining the presence of IBS when the level of anti-vinculin antibodies is higher than the level of anti-CDT antibodies.

Various embodiments of the present invention provide for a method of distinguishing between IBS and IBD, comprising: providing a biological sample from a subject desiring a diagnosis to distinguish between IBS and IBD; assaying the biological sample for a level of anti-vinculin antibodies and a level of anti-CDT antibodies; determining the difference between the level of anti-vinculin antibodies and the level of anti-CDT antibodies; and determining the presence of IBS when the level of anti-vinculin antibodies is higher than the level of anti-CDT antibodies.

In various embodiments, the assay comprises adding vinculin or a fragment thereof as discussed herein and CdtB or a fragment thereof as described herein to a biological sample from a subject desiring a determination regarding IBS, wherein anti-vinculin and/or anti-CdtB antibodies (if present in the biological sample) specifically binds to the vinculin or the fragment thereof and/or the CdtB or the fragment thereof in the biological sample; measuring the levels the anti-vinculin antibodies and the anti-CdtB antibodies in the biological sample; and identifying that the subject has IBS if the level of the anti-vinculin antibodies is higher than the level of the anti-CdtB antibodies. In various embodiments, the assay can be two separate assays, one to detect the level of anti-vinculin antibodies and one to detect the level of anti-CdtB antibodies. In various embodiments, the assay can be a single assay that detects both anti-vinculin and anti-CdtB antibodies.

In various embodiments, the subject is determined to have IBS if the level of anti-vinculin antibodies is 1, 2, 3, 4, 5, 6, 7, 8, 9, 10, 15, 20, 25, 30, 45, 50, 55, 60, 65, 70, 75, 80, 85, 90, 95, 100, 125, 150, 175, 200, 250, 300, 350, 400, 450, 500, 600, 700, 800, 900, or 1000% or more higher than the level of anti-CDT antibodies.

In various embodiments, the extent of the level of anti-vinculin antibodies that is greater than anti-CDT antibodies provides a positive predictive value regarding the presence of IBS. The percentage in relation to the positive predictive value can be as described herein. In some embodiments, the percentage in relation to the positive predictive value can be calculated by examining additional IBS patients vs. controls or additional IBS patients vs. IBD patients for their levels of anti-vinculin antibodies and anti-CDT antibodies.

In certain embodiments, optical density (OD) is used to measure the level of anti-vinculin antibodies and anti-CDT antibodies. Thus, when the difference between the OD of anti-vinculin antibodies ($OD_V$) and the OD of anti-CDT antibodies ($OD_{CDT}$) is greater than 0, the subject is determined to have IBS. In various embodiments, when $OD_V - OD_{CDT}$ is greater than 0.1, 0.2, 0.3, 0.4, 0.5, or 0.6, the subject is determined to have IBS. In certain embodiments, when $OD_V - OD_{CDT}$ is greater than 0.2, the subject is determined to have IBS. In various embodiments, the extent of $OD_V - OD_{CDT}$ provides a positive predictive value regarding the presence of IBS. The $OD_V - OD_{CDT}$ value in relation to the positive predictive value can be as described herein. In some embodiments, the $OD_V - OD_{CDT}$ value in relation to the positive predictive value can be calculated by examining additional IBS patients vs. controls or additional IBS patients vs. IBD patients for their levels of anti-vinculin antibodies and anti-CDT antibodies.

In various embodiments, a 96-well plate is coated overnight or >16 hours at about 4° C. in a humidified box with about 100 µl/well of antigen (vinculin or CdtB) @ about 1.2 µg/ml in BBS, approximate pH is 8.2. An additional well is coated, with each sample, with only BBS to determine non-specific background due to serum that will be subtracted from antigen coated well. Wells are washed about 3 times with approximately 250 µl/well of 0.05% PBS-T. Wells are blocked with about 200 µl/well of about 3% BSA in PBS for about 1 hour at room temperature in a humidified box. Sera are diluted to a 1:16 dilution using about 3% BSA in PBS. About 100 µl/well of serum are added; and incubated for about 1 hour at room temperature in humidified box. Wells are washed about 3 times with approximately 250 µl/well of 0.05% PBS-T About 100 µl/well of an about 1:10,000 secondary antibody conjugated to HRP diluted in about 3% BSA in PBS is added. It is incubated for 1 hr at room temperature in humidified box. Wells are washed about 6 times with approximately 250 µl/well of about 0.05% PBS-T 100 µl/well of TMB substrate solution (1-Step Ultra TMB-ELISA Substrate, Pierce, 34028) is added. Plate is immediately read on plate reader (e.g., BioTek Synergy HT) using an absorbance protocol at about 370 nm; and is allowed to develop for about 90 min (assay plateaus around 60 min.).

In various embodiments, the IBS can be C-IBS, D-IBS, A-IBS (also known as M-IBS). In various embodiments, the IBS is severe IBS. In various embodiments, the IBS is severe C-IBS, severe-D-IBS, or severe A-IBS.

In various embodiments, the anti-CDT antibodies are anti-CdtB antibodies.

In various embodiments, the assays comprise vinculin or a fragment thereof as discussed herein and CdtB or a fragment thereof as discussed herein as the antigen to detect anti-vinculin and anti-CdtB antibodies.

Systems

Various embodiments of the present invention provide for a system to diagnose IBS comprising: an isolated biological sample from a subject desiring a diagnosis regarding IBS; and one or more assays for detecting a level of anti-vinculin antibodies and a level of anti-CDT antibodies to diagnose IBS.

Various embodiments of the present invention provide for a system to distinguish between IBS and IBD, comprising: an isolated biological sample from a subject desiring a diagnosis to distinguish between IBS and IBD; one or more assays to detect a level of anti-vinculin antibodies and a level of anti-CDT antibodies to distinguish between IBS and IBD.

In various embodiments, these systems further comprise a machine for determining a presence of IBS when the level of anti-vinculin antibodies is higher than the level of anti-CDT antibodies.

In various embodiments, the system comprises an output or display element for displaying whether the patient has IBS, and/or for displaying whether the anti-vinculin antibodies is higher than the level of anti-CDT antibodies.

In various embodiments, the system determines that the subject has IBS if the level of anti-vinculin antibodies is 1, 2, 3, 4, 5, 6, 7, 8, 9, 10, 15, 20, 25, 30, 45, 50, 55, 60, 65, 70, 75, 80, 85, 90, 95, 100, 125, 150, 175, 200, 250, 300, 350, 400, 450, 500, 600, 700, 800, 900, or 1000% or more higher than the level of anti-CDT antibodies. In various embodiments, the extent of the level of anti-vinculin antibodies that is greater than anti-CDT antibodies provides a positive predictive value regarding the presence of IBS. The percentage in relation to the positive predictive value can be as described herein. In some embodiments, the percentage in relation to the positive predictive value can be calculated by examining additional IBS patients vs. controls or additional IBS patients vs. IBD patients for their levels of anti-vinculin antibodies and anti-CDT antibodies.

In certain embodiments, optical density (OD) is used to measure the level of anti-vinculin antibodies and anti-CDT antibodies. Thus, when the difference between the OD of anti-vinculin antibodies ($OD_V$) and OD of anti-CDT antibodies ($OD_{CDT}$) is greater than 0, the system determines that the subject has IBS. In various embodiments, when $OD_V-OD_{CDT}$ is greater than 0.1, 0.2, 0.3, 0.4, 0.5, or 0.6, the system determines that the subject has IBS. In certain embodiments, when $OD_V-OD_{CDT}$ is greater than 0.2, the subject is determined to have IBS. In various embodiments, the extent of $OD_V-OD_{CDT}$ provides a positive predictive value regarding the presence of IBS. The $OD_V-OD_{CDT}$ value in relation to the positive predictive value can be as described herein. In some embodiments, the $OD_V-OD_{CDT}$ value in relation to the positive predictive value can be calculated by examining additional IBS patients vs. controls or additional IBS patients vs. IBD patients for their levels of anti-vinculin antibodies and anti-CDT antibodies.

In various embodiments, the IBS can be C-IBS, D-IBS, A-IBS (also known as M-IBS). In various embodiments, the IBS is severe IBS. In various embodiments, the IBS is severe C-IBS, severe-D-IBS, or severe A-IBS.

In various embodiments, the anti-CDT antibodies are anti-CdtB antibodies.

In various embodiments, the assays comprise vinculin or a fragment thereof as discussed herein and CdtB or a fragment thereof as discussed herein as the antigen to detect anti-vinculin and anti-CdtB antibodies.

Non-Human Machines/Computer Implementation Systems and Methods

Various embodiments of the present invention provides for a non-transitory computer readable medium comprising instructions to execute the methods of the present invention, as described herein.

In certain embodiments, the methods of the invention implement a computer program for example, to compare the levels of anti-vinculin antibodies and the levels of anti-CDT antibodies. For example, a non-transitory computer program can be used to perform the algorithms described herein.

Numerous types of computer systems can be used to implement the analytic methods of this invention according to knowledge possessed by a skilled artisan in the bioinformatics and/or computer arts.

Several software components can be loaded into memory during operation of such a computer system. The software components can comprise both software components that are standard in the art and components that are special to the present invention. The methods of the invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or 5-Plus from MathSoft (Seattle, Wash.). In certain embodiments, the computer comprises a database for storage of levels of anti-vinculin antibodies and levels of anti-CDT antibodies. Such stored profiles can be accessed and used to compare levels of anti-vinculin antibodies and levels of anti-CDT antibodies in the sample to known control levels, if applicable.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

Once a laboratory technician or laboratory professional or group of laboratory technicians or laboratory professionals determines the level of anti-vinculin antibodies and the level of anti-CDT antibodies, the same or a different laboratory technician or laboratory professional (or group) can analyze one or more assays to determine whether the level of anti-vinculin antibodies is higher than the level of anti-CDT antibodies or whether the $OD_V-OD_{CDT}$ is greater than 0.0, 0.1, 0.2, 0.3, 0.4, 0.5, or 0.6 and then determine that the subject has IBS or severe IBS.

In various embodiments, provided herein is a non-transitory computer readable storage medium comprising: a storing data module containing data from a sample comprising a level of anti-vinculin antibodies and a level of anti-CDT antibodies; a detection module to detect the level of anti-vinculin antibodies and the level of anti-CDT antibodies; a comparison module that compares the data stored on the storing data module with a reference data and/or control data, or a comparison module to compare the level of anti-vinculin antibodies to the level of anti-CDT antibodies and to provide a comparison content, and an output module displaying the comparison content for the user, wherein an indication that the subject has IBS is displayed when the level of anti-vinculin antibodies is greater than the level of anti-CDT antibodies, or when the $OD_V-OD_{CDT}$ is greater than 0.0, 0.1, 0.2, 0.3, 0.4, 0.5, or 0.6.

In various embodiments, the control data comprises data from patients who do not have IBS. In various embodiments, the control data comprises data from patients who do not have IBD. In various embodiments, the control data comprises data from patients who have IBS. In various embodiments, the control data comprises data from patients who have IBD.

Embodiments of the invention can be described through functional modules, which are defined by computer executable instructions recorded on a non-transitory computer readable media and which cause a computer to perform method steps when executed. The modules are segregated by function, for the sake of clarity. However, it should be understood that the modules/systems need not correspond to discreet blocks of code and the described functions can be carried out by the execution of various code portions stored on various media and executed at various times. Furthermore, it should be appreciated that the modules may perform other functions, thus the modules are not limited to having any particular functions or set of functions.

The non-transitory computer readable storage media can be any available tangible media that can be accessed by a computer. Computer readable storage media includes volatile and nonvolatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (eraseable programmable read only memory), EEPROM (electrically eraseable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can be accessed by a computer including and any suitable combination of the foregoing.

Computer-readable data embodied on one or more non-transitory computer-readable media may define instructions, for example, as part of one or more programs that, as a result of being executed by a computer, instruct the computer to perform one or more of the functions described herein, and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media on which such instructions are embodied may reside on one or more of the components of either of a system, or a computer readable storage medium described herein, may be distributed across one or more of such components.

The computer-readable media may be transportable such that the instructions stored thereon can be loaded onto any computer resource to implement the aspects of the present invention discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a computer to implement aspects of the present invention. The computer executable instructions may be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

The functional modules of certain embodiments of the invention, include for example, a measuring module, a storage module, a comparison module, and an output module. The functional modules can be executed on one, or multiple, computers, or by using one, or multiple, computer networks. The measuring module has computer executable instructions to provide, e.g., expression information in computer readable form.

The measuring module, can comprise any system for detecting the levels of anti-vinculin antibodies or anti-CDT antibodies.

The information determined in the determination system can be read by the storage module. As used herein the "storage module" is intended to include any suitable computing or processing apparatus or other device configured or adapted for storing data or information. Examples of electronic apparatus suitable for use with the present invention include stand-alone computing apparatus, data telecommunications networks, including local area networks (LAN), wide area networks (WAN), Internet, Intranet, and Extranet, and local and distributed computer processing systems. Storage modules also include, but are not limited to: magnetic storage media, such as floppy discs, hard disc storage media, flash drives, magnetic tape, optical storage media such as CD-ROM, DVD, electronic storage media such as RAM, ROM, EPROM, EEPROM and the like, general hard disks and hybrids of these categories such as magnetic/optical storage media. The storage module is adapted or configured for having recorded thereon the level of anti-vinculin antibodies and level of anti-CDT antibodies information. Such information may be provided in digital form that can be transmitted and read electronically, e.g., via the Internet, on a flash drive, via USB (universal serial bus) or via any other suitable mode of communication.

As used herein, "stored" refers to a process for encoding information on the storage module. Those skilled in the art can readily adopt any of the presently known methods for recording information on known media to generate manufactures comprising anti-vinculin antibody level and anti-CDT antibody level information.

In one embodiment the reference data stored in the storage module to be read by the comparison module is, e.g., data from patients who do not have IBS, data from patients who do not have IBD, data from patients who have IBS, and/or data from patients who have IBD.

The "comparison module" can use a variety of available software programs and formats for the comparison operative to compare binding data determined in the measuring module to reference samples and/or stored reference data. In one embodiment, the comparison module is configured to use pattern recognition techniques to compare information from one or more entries to one or more reference data patterns. The comparison module may be configured using existing commercially-available or freely-available software for comparing patterns, and may be optimized for particular data comparisons that are conducted. The comparison module provides computer readable information related, for example, anti-vinculin antibody levels and/or anti-CDT antibody levels.

The comparison module, or any other module of the invention, may include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in a particular embodiment of the present invention, users can directly access data (via Hypertext links for example) residing on Internet databases using a HTML interface provided by Web browsers and Web servers.

The comparison module provides a computer readable comparison result that can be processed in computer readable form by predefined criteria, or criteria defined by a user, to provide a content-based in part on the comparison result that may be stored and output as requested by a user using an output module.

The content based on the comparison result, may be anti-vinculin antibody levels compared to anti-CDT antibody levels.

In various embodiments of the invention, the content based on the comparison result is displayed on a computer monitor. In various embodiments of the invention, the content based on the comparison result is displayed through printable media. The display module can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content based on the comparison result. It should be understood that other modules of the invention can be adapted to have a web browser interface. Through the Web browser, a user may construct requests for retrieving data from the comparison module. Thus, the user will typically point and click to user interface elements such as buttons, pull down menus, scroll bars and the like conventionally employed in graphical user interfaces.

Biological Samples

Examples of biological samples include but are not limited to body fluids, whole blood, plasma, stool, intestinal fluids or aspirate, and stomach fluids or aspirate, serum, cerebral spinal fluid (CSF), urine, sweat, saliva, tears, pulmonary secretions, breast aspirate, prostate fluid, seminal fluid, cervical scraping, amniotic fluid, intraocular fluid, mucous, and moisture in breath. In particular embodiments of the method or system, the biological sample may be whole blood, blood plasma, blood serum, stool, intestinal fluid or aspirate or stomach fluid or aspirate. In certain embodiments, the biological sample is whole blood. In certain embodiments, the biological sample is serum. In certain embodiments, the biological sample is plasma.

Anti-Vinculin Antibodies

In various embodiments, the anti-vinculin antibody detected in these methods, assays, or systems is an antibody that binds specifically to vinculin.

In various embodiments, the anti-vinculin antibody is an antibody that binds specifically to a 5, 6, 7, 8, 9, 10, 11, 12, 13, 14, 15, 16, 17, 18, 19, 20, 21, or 22 residue peptide that has at least 95%, 96%, 97%, 98%, 99% or 100% homology with 5, 6, 7, 8, 9, 10, 11, 12, 13, 14, 15, 16, 17, 18, 19, 20, 21, or 22 contiguous residues of vinculin.

In another embodiment, the anti-vinculin antibody binds specifically to a polypeptide comprising 5, 6, 7, 8, 9, 10, 11, 12, 13, 14, 15, 16, 17, 18, 19, 20, 21, or 22 residues that has at least 95%, 96%, 97%, 98%, 99% or 100% homology with 5, 6, 7, 8, 9, 10, 11, 12, 13, 14, 15, 16, 17, 18, 19, 20, 21, or 22 contiguous residues of vinculin.

In another embodiment, the anti-vinculin antibody binds specifically to a polypeptide comprising or consisting of 5, 6, 7, 8, 9, 10, 11, 12, 13, 14, 15, 16, 17, 18, 19, 20, 21, or 22 contiguous residues of vinculin.

In various embodiments, the anti-vinculin antibody is an antibody that binds specifically to SEQ ID NO:7.

In various embodiments, the anti-vinculin antibody is an antibody that binds specifically to a 5, 6, 7, 8, 9, 10, 11, 12, 13, 14, 15, 16, 17, 18, 19, 20, 21, or 22 residue peptide that has at least 95%, 96%, 97%, 98%, 99% or 100% homology with 5, 6, 7, 8, 9, 10, 11, 12, 13, 14, 15, 16, 17, 18, 19, 20, 21, or 22 contiguous residues of SEQ ID NO:7.

In another embodiment, the anti-vinculin antibody binds specifically to a polypeptide comprising 5, 6, 7, 8, 9, 10, 11, 12, 13, 14, 15, 16, 17, 18, 19, 20, 21, or 22 residues that has at least 95%, 96%, 97%, 98%, 99% or 100% homology with 5, 6, 7, 8, 9, 10, 11, 12, 13, 14, 15, 16, 17, 18, 19, 20, 21, or 22 contiguous residues of SEQ ID NO:7.

In another embodiment, the anti-vinculin antibody binds specifically to a polypeptide comprising or consisting of 5, 6, 7, 8, 9, 10, 11, 12, 13, 14, 15, 16, 17, 18, 19, 20, 21, or 22 contiguous residues of SEQ ID NO:7.

Contiguous residues of vinculin or SEQ ID NO:7 include those beginning at any amino acid and ending at any amino acid of vinculin or SEQ ID NO:7.

Protein sequence of Vinculin (SEQ ID NO:7):

```
MPVFHTRTIESILEPVAQQISHLVIMHEEGEVDGKAIPDLTAPVAAVQAA

VSNLVRVGKETVQTTEDQILKRDMPPAFIKVENACTKLVQAAQMLQSDPY

SVPARDYLIDGSRGILSGTSDLLLTFDEAEVRKIIRVCKGILEYLTVAEV

VETMEDLVTYTKNLGPGMTKMAKMIDERQQELTHQEHRVMLVNSMNTVKE

LLPVLISAMKIFVTTKNSKNQGIEEALKNRNFTVEKMSAEINEIIRVLQL

TSWDEDAWASKDTEAMKRALASIDSKLNQAKGWLRDPSASPGDAGEQAIR

QILDEAGKVGELCAGKERREILGTCKMLGQMTDQVADLRARGQGSSPVAM

QKAQQVSQGLDVLTAKVENAARKLEAMTNSKQSIAKKIDAAQNWLADPNG

GPEGEEQIRGALAEARKIAELCDDPKERDDILRSLGEISALTSKLADLRR

QGKGDSPEARALAKQVATALQNLQTKTNRAVANSRPAKAAVHLEGKIEQA

QRWIDNPTVDDRGVGQAAIRGLVAEGHRLANVMMGPYRQDLLAKCDRVDQ

LTAQLADLAARGEGESPQARALASQLQDSLKDLKARMQEAMTQEVSDVFS

DTTTPIKLLAVAATAPPDAPNREEVFDERAANFENHSGKLGATAEKAAAV

GTANKSTVEGIQASVKTARELTPQVVSAARILLRNPGNQAAYEHFETMKN

QWIDNVEKMTGLVDEAIDTKSLLDASEEAIKKDLDKCKVAMANIQPQMLV

AGATSIARRANRILLVAKREVENSEDPKFREAVKAASDELSKTISPMVMD

AKAVAGNISDPGLQKSFLDSGYRILGAVAKVREAFQPQEPDFPPPPPDLE

QLRLTDELAPPKPPLPEGEVPPPRPPPPEEKDEEFPEQKAGEVINQPMMM

AARQLHDEARKWSSKGNDIIAAAKRMALLMAEMSRLVRGGSGTKRALIQC

AKDIAKASDEVTRLAKEVAKQCTDKRIRTNLLQVCERIPTISTQLKILST

VKATMLGRTNISDEESEQATEMLVHNAQNLMQSVKETVREAEAASIKIRT

DAGFTLRWVRKTPWYQ
```

Anti-CDT Antibodies

In various embodiments, the anti-CDT antibody an antibody that binds specifically to CDT. The amino acid sequences of CDT are known in the art.

In one embodiment, the anti-CDT antibody specifically binds to an epitope on the receptor-binding domain of CDT.

In another embodiment, the anti-CDT antibody binds specifically to the CdtA subunit of CDT. In another embodiment, the anti-CDT antibody binds specifically to the CdtB subunit of CDT. In another embodiment, the anti-CDT antibody binds specifically to the CdtC subunit of CDT.

An example of a CdtB amino acid sequence is *Campylobacter jejuni* cytolethal distending toxin B, which has the amino acid sequence (SEQ ID NO: 5).

SEQ ID NO:5 (CdtB of *Campylobacter jejuni*):

MKKIICLFLSFNLAFANLENFNVGTWNLQGSSAATESKWSVSVRQLVSGA

NPLDILMIQEAGTLPRTATPTGRHVQQGGTPIDEYEWNLGTLSRPDRVFI

YYSRVDVGANRVNLAIVSRMQAEEVIVLPPPTTVSRPIIGIRNGNDAFFN

IHALANGGTDVGAIITAVDAHFANMPQVNWMIAGDFNRDPSTITSTVDRE

LANRIRVVFPTSATQASGGTLDYAITGNSNRQQTYTPPLLAAILMLASLR

SHIVSDHFPVNFRKF

Another example of a CdtB amino acid sequence is *Campylobacter coli* cytolethal distending toxin B, which has the amino acid sequence (SEQ ID NO: 1) and nucleic acid sequence (SEQ ID NO:2).

SEQ ID NO:1 (amino acid sequence of CdtB of *Campylobacter Coli*):

MKKIVFLILSFNVLFAALENYNTGTWNLQGSSAATESKWNVSIRQLITGA

NPMDVLAVQEAGVLPSTAMMTPRQVQPVGVGIPIHEYIWNLGSVSRPSSV

YIYYSRVDVGANRVNLAIVSRVQADEVFVLPPPTVASRPIIGIRIGNDAF

FNIHALASGGNDAGAIVAAVDMFFRNRPDINWMILGDFNRESGALVTLLD

PDLRARTRVVVPPSSTQTSGRTIDYAITGNSNTAALYNPPPIVAILALEG

LRTFLASDHFPVNFRRP

SEQ ID NO:2 (nucleic acid sequence of CdtB of *Campylobacter Coli*):

```
atgaaaaaaa tagtattttt gattttaagt tttaatgtat tatttgccgc tttagaaaat tacaacaccg gaacttggaa tttgcaaggc tcatcagctg caactgaaag caaatggaat gttagtataa gacaactcat aaccggtgca aatcctatgg atgttttagc tgttcaagaa gcggggggttt tacctagtac agctatgatg actcctagac aggtacaacc cgtgggcgtg ggtattccta tacatgaata catatggaat ttaggctctg tatcaagacc tagctctgtt tatatatatt attctagagt ggatgtagga gcaaatcgtg tgaatttagc tatcgttagc agagtgcaag cggatgaagt ttttgtttta cccccctccaa cagttgcttc aagacctatt ataggcatac gcataggcaa tgatgctttt ttcaatatac acgctctagc aagtgggga aatgacgcag gagccattgt cgctgctgtg gatatgtttt ttagaaatag acctgatatt aattggatga ttttaggcga tttttaataga gaatcaggcg ccttagtaac cttgctagat cctgacttaa gagcacgcac tcgcgtagtt gttccgcctt cttctacgca aacaagtgga agaacgattg attatgctat cactggaaat tccaacactg cagctttata caacccacca
```

-continued
```
ccgatagttg cgattttagc tttagaagga ttaagaacct tttggcttc agatcatttt cctgtaaatt ttagaagacc ttag
```

Accordingly, in one embodiment, the anti-CDT antibody binds specifically to SEQ ID NO:5 (CdtB of *C. jejuni*). In various embodiments, the anti-CDT antibody binds specifically to an amino acid sequence at least 80%, 85%, 90%, 95%, 96%, 97%, 98%, or 99% identical to SEQ ID NO: 5.

In another embodiment, the anti-CDT antibody binds specifically to SEQ ID NO:1 (CdtB of *C. coli*). In various embodiments, the anti-CDT antibody binds specifically to an amino acid sequence at least 80%, 85%, 90%, 95%, 96%, 97%, 98%, or 99% identical to SEQ ID NO: 1.

In another embodiment, the anti-CDT antibody binds specifically to a 17 residue peptide of CdtB (e.g., 17 residues of SEQ. ID NOs: 1 or 5). In one embodiment, the 17 residue peptide has the following sequence: LDYAITGNSNRQQTYTP (SEQ ID NO:3).

In other embodiments, the anti-CDT antibody binds specifically to a 17 residue peptide that has at least 80%, 85%, 90%, 95%, 96%, 97%, 98%, 99% or 100% homology with 17 contiguous residues of CdtB (e.g., 17 contiguous residues of SEQ. ID NOs: 1 or 5). In one embodiment, the 17 residues of CdtB have the following sequence: LDYAITGNSNRQQTYTP (SEQ ID NO:3).

In other embodiments, the anti-CDT antibody binds specifically to a polypeptide comprising 17 residues that have at least 80%, 85%, 90%, 95%, 96%, 97%, 98%, 99% or 100% homology with 17 contiguous residues of CdtB (e.g., 17 residues of SEQ. ID NOs: 1 or 5). In one embodiment, the 17 contiguous residues of CdtB have the following sequence: LDYAITGNSNRQQTYTP (SEQ ID NO:3).

In another embodiment, the anti-CDT antibody binds specifically to an 18 residue peptide having the following sequence: CLDYAITGNSNRQQTYTP (SEQ ID NO:4). The cysteine at the N-terminus was added to SEQ ID NO:3 for purposes of conjugation.

In other embodiments, the anti-CDT antibody binds specifically to a polypeptide comprising 18 residues that have at least 80%, 85%, 90%, 95%, 96%, 97%, 98%, 99% or 100% homology to CLDYAITGNSNRQQTYTP (SEQ ID NO:4).

In another embodiment, the anti-CDT antibody binds specifically to a 5, 6, 7, 8, 9, 10, 11, 12, 13, 14, 15, 16, 17, 18, 19, 20, 21, or 22 residue peptide that has at least 80%, 85%, 90%, 95%, 96%, 97%, 98%, 99% or 100% homology with 5, 6, 7, 8, 9, 10, 11, 12, 13, 14, 15, 16, 17, 18, 19, 20, 21, or 22 contiguous residues of CdtB (e.g., 5, 6, 7, 8, 9, 10, 11, 12, 13, 14, 15, 16, 17, 18, 19, 20, 21, or 22 contiguous residues of SEQ ID NOs:1 or 5). In another embodiment, the anti-CDT antibody binds specifically to a polypeptide comprising 5, 6, 7, 8, 9, 10, 11, 12, 13, 14, 15, 16, 17, 18, 19, 20, 21, or 22 residues that has at least 80%, 85%, 90%, 95%, 96%, 97%, 98%, 99% or 100% homology with 5, 6, 7, 8, 9, 10, 11, 12, 13, 14, 15, 16, 17, 18, 19, 20, 21, or 22 contiguous residues of CdtB (e.g., 5, 6, 7, 8, 9, 10, 11, 12, 13, 14, 15, 16, 17, 18, 19, 20, 21, or 22 contiguous residues of SEQ ID NOs:1 or 5). Contiguous residues of SEQ ID NO:1 include those beginning at any amino acid and ending at any amino acid of SEQ ID NO:1. Contiguous residues of SEQ ID NO:5 include those beginning at any amino acid and ending at any amino acid of SEQ ID NO:5.

In another embodiment, the anti-CDT antibody binds specifically to a 5, 6, 7, 8, 9, 10, 11, 12, 13, 14, 15, 16, or 17 residue peptide that has at least 80%, 85%, 90%, 95%, 96%, 97%, 98%, 99% or 100% homology with 5, 6, 7, 8, 9, 10, 11, 12, 13, 14, 15, 16, or 17 contiguous residues of LDYAITGNSNRQQTYTP (SEQ ID NO:3) (e.g., 5, 6, 7, 8, 9, 10, 11, 12, 13, 14, 15, 16, or 17 contiguous residues of SEQ ID NO:3). In another embodiment, the anti-CDT antibody binds specifically to a polypeptide comprising 5, 6, 7, 8, 9, 10, 11, 12, 13, 14, 15, 16, or 17 residues that has at least 80%, 85%, 90%, 95%, 96%, 97%, 98%, 99% or 100% homology with 5, 6, 7, 8, 9, 10, 11, 12, 13, 14, 15, 16, or 17 contiguous residues of SEQ ID NO:3 (e.g., 5, 6, 7, 8, 9, 10, 11, 12, 13, 14, 15, 16, or 17 contiguous residues of SEQ ID NO:3). Contiguous residues of SEQ ID NO: 3 include those beginning at any amino acid and ending at any amino acid of SEQ ID NO: 3.

In another embodiment, the anti-CDT antibody binds specifically to a 17 residue peptide encoded by the CdtB gene sequence. In particular embodiments, the purified antibody binds specifically to a 17 residue peptide encoded by SEQ ID NO: 2. In various embodiments, the anti-CDT antibody binds specifically to a 14, 15, 16, 17, 18, 19, 20, 21, or 22 residue peptide encoded by SEQ ID NO: 2. In various embodiments, the anti-CDT antibody binds specifically to a 14, 15, 16, 17, 18, 19, 20, 21, or 22 residue peptide that has at least 80%, 85%, 90%, 95%, 96%, 97%, 98%, 99% or 100% homology to 14, 15, 16, 17, 18, 19, 20, 21, or 22 contiguous residues encoded by SEQ ID NO: 2. In various embodiments, the anti-CDT antibody binds specifically to a polypeptide comprising 14, 15, 16, 17, 18, 19, 20, 21, or 22 residues that have at least 80%, 85%, 90%, 95%, 96%, 97%, 98%, 99% or 100% homology to 14, 15, 16, 17, 18, 19, 20, 21, or 22 contiguous residues encoded by SEQ ID NO: 2.

In another embodiment, the anti-CDT antibody binds specifically to a peptide encoded by the nucleic acid sequence having the following sequence: CTTGATTATG-CAATTACAGGAAATTCAAATAGACAACAAAC-CTATACTCCA (SEQ ID NO:6), which encodes the 17 amino acid peptide of SEQ ID NO. 3. In another embodiment, the anti-CDT antibody binds specifically to a polypeptide comprising a peptide encoded by SEQ ID NO:6.

In another embodiment, the anti-CDT antibody binds specifically to CdtB purified from E. coli overexpressing a near full-length CdtB ORF. (See Infection and Immunity, December 2000, p. 6535-6541, Vol. 68, No. 12, herein incorporated by reference in its entirety as though fully set forth.)

Assays

In various embodiments of the methods and systems described herein, the assay is an enzyme-linked immunosorbent assay (ELISA), including but not limited to indirect ELISA, sandwich ELISA, competitive ELISA, multiple and portable ELISA.

In various embodiments of the methods and systems described herein, the assay is an assay to detect the level of anti-vinculin antibodies. The assay can comprise: a first reagent (e.g., the antigen) to react with the biological sample if the biological sample comprises the anti-vinculin antibody (if anti-vinculin antibodies are not present, then the first reagent will not react the biological sample, but the first reagent is still present in the assay), a second reagent (e.g., secondary antibody) to react with the anti-vinculin antibody or a second reagent to react with the first reagent, and a substrate (e.g., to react with the second reagent and produce a signal). In various embodiments, the first reagent is vinculin, SEQ ID NO:7 or a fragment thereof as discussed herein. In various embodiments, the second reagent comprises a label to produce a signal to indicate the presence of the anti-vinculin antibody. In various embodiments, the label is a radiolabel, a chromophore, a fluorophore, a quantum dot, an enzyme, horseradish peroxidase (HRP), an alkaline phosphatase (AP), biotin, or a combination thereof. In various embodiments, the label is an enzyme that will react with the substrate. In various embodiments, the first reagent is on a solid phase (e.g., plate, multi-well plate). In various embodiments the substrate is a chromogenic substrate (e.g., 3,3',5,5'-Tetramethylbenzidine (TMB), 3,3'-Diaminobenzidine (DAB), 2,2-azino-bis(3-ethylbenzothiazoline-6-sulphonic acid) (ABTS). In various embodiments, the substrate is a chemiluminescence substrate (e.g., ECL).

In various embodiments, the assay comprises a first reagent to react with the anti-vinculin antibody. In various embodiments, the first reagent comprises a label to produce a signal to indicate the presence of the anti-vinculin antibody. In various embodiments, the label is a radiolabel, a chromophore, a fluorophore, a quantum dot, an enzyme, horseradish peroxidase (HRP), an alkaline phosphatase (AP), biotin, or a combination thereof. In various embodiments, the first reagent is on a solid phase (e.g., plate, multi-well plate). In various embodiments, the assay further comprises a substrate to react with the label in instances wherein the label requires a substrate to produce the signal; for example HRP can be reacted with the substrate TMB.

In various embodiments, the assay is an assay to determine the level of anti-CDT antibodies. The assay can comprise: a first reagent to react with the biological sample if the biological sample comprises the anti-CDT antibody (if anti-CDT antibodies are not present, then the first reagent will not react the biological sample, but the first reagent is still present in the assay), a second reagent (e.g., secondary antibody) to react with the anti-CDT antibody or a second reagent to react with the first reagent, and a substrate. In various embodiments, the first reagent is CDT, CdtA, CdtB, CdtC, SEQ ID NOs: 1, 2, 4, 5 or a fragment thereof as discuss herein. In various embodiments, the second reagent comprises a label to produce a signal to indicate the presence of the anti-CDT antibody. In various embodiments, the label is a radiolabel, a chromophore, a fluorophore, a quantum dot, an enzyme, horseradish peroxidase (HRP), an alkaline phosphatase (AP), biotin, or a combination thereof. In various embodiments, the label is an enzyme that will react with the substrate. In various embodiments, the first reagent is on a solid phase (e.g., plate, multi-well plate). In various embodiments the substrate is a chromogenic substrate (e.g., 3,3',5,5'-Tetramethylbenzidine (TMB), 3,3'-Diaminobenzidine (DAB), 2,2'-azino-bis(3-ethylbenzothiazoline-6-sulphonic acid) (ABTS). In various embodiments, the substrate is a chemiluminescence substrate (e.g., ECL).

In various embodiments, the assay comprises a first reagent to react with the anti-CDT antibody. In various embodiments, the first reagent comprises a label to produce a signal to indicate the presence of the anti-CDT antibody. In various embodiments, the label is a radiolabel, a chromophore, a fluorophore, a quantum dot, an enzyme, horseradish peroxidase (HRP), an alkaline phosphatase (AP), biotin, or a combination thereof. In various embodiments, the reagent is on a solid phase (e.g., plate, multi-well plate). In various embodiments, the assay further comprises a substrate to react with the label in instances wherein the label requires a substrate to produce the signal; for example HRP can be reacted with the substrate TMB.

In various embodiments, the assay is an assay to determine the level of the anti-vinculin antibodies and the level anti-CDT antibodies. The assay can comprise: a first reagent and second reagent to react with the biological sample if the biological sample comprises the anti-vinculin antibody and/ or the anti-CDT antibody (if anti-vinculin antibodies are not present, then the first reagent will not react with the biological sample, but the first reagent is still present in the assay; or if anti-CDT antibodies are not present, then the second reagent will not react with the biological sample, but the second reagent is still present in the assay), a third reagent and a fourth (e.g., secondary antibodies) to react with the anti-vinculin antibody, the anti-CDT antibody, or a third reagent to react with the first reagent, and a fourth reagent to react with the second reagent, and a substrate. In various embodiments, the first reagent is vinculin or a fragment thereof. In various embodiments, the second reagent is CDT or a fragment thereof. In various embodiments, the third reagent and/or the fourth reagent comprises a label to produce a signal to indicate the presence of the anti-vinculin antibody and/or the anti-CDT antibody. In various embodiments, the label is a radiolabel, a chromophore, a fluorophore, a quantum dot, an enzyme, horseradish peroxidase (HRP), an alkaline phosphatase (AP), biotin, or a combination thereof. In various embodiments, the label is an enzyme that will react with the substrate. In various embodiments, the first reagent is on a solid phase (e.g., plate, multi-well plate). In various embodiments the substrate is a chromogenic substrate (e.g., 3,3',5,5'-Tetramethylbenzidine (TMB), 3,3'-Diaminobenzidine (DAB), 2,2'-azino-bis(3-ethylbenzothiazoline-6-sulphonic acid) (ABTS). In various embodiments, the substrate is a chemiluminescence substrate (e.g., ECL).

In various embodiments, the assay comprises a first reagent to react with the anti-vinculin antibody and a second reagent to react with the anti-CDT antibody. In various embodiments, the first reagent and/or the second reagent comprises a label to produce a signal to indicate the presence of the anti-vinculin antibody and/or anti-CDT antibody. In various embodiments, the label is a radiolabel, a chromophore, a fluorophore, a quantum dot, an enzyme, horseradish peroxidase (HRP), an alkaline phosphatase (AP), biotin, or a combination thereof. In various embodiments, the reagent is on a solid phase (e.g., plate, multi-well plate). In various embodiments, the assay further comprises a substrate to react with the label in instances wherein the label requires a substrate to produce the signal; for example HRP can be reacted with the substrate TMB.

In various embodiments, detecting the level of the anti-vinculin antibody or the level of anti-CDT antibody is performed on a biological sample obtained from the subject. In another embodiment, detecting the level of the anti-vinculin antibody or the level of anti-CDT antibody is performed on a blood, serum, or stool sample obtained from the subject. One of ordinary skill in the art will readily appreciate methods and systems that can be used to detect the level of the anti-vinculin antibody or the level of anti-CDT antibody. These methods and systems include but are not limited to ELISA, immunohistochemistry, flow cytometry, fluorescence in situ hybridization (FISH), radioimmuno assays, and affinity purification.

In various embodiments, vinculin, SEQ ID NO: 7 or a fragment thereof (as described above) is used as a reagent (e.g., collector, trap) to bind anti-vinculin antibodies (if present).

In certain embodiments, detecting the level an antibody that binds specifically to vinculin, SEQ ID NO: 7 or a fragment thereof may be performed by contacting vinculin, SEQ ID NO: 7 or a fragment thereof to a biological sample obtained from the subject to isolate the antibody that binds specifically to vinculin, SEQ ID NO: 7 or a fragment thereof.

In various embodiments, the fragment of vinculin or SEQ ID NO: 7 may be the fragments as described herein. As an example, an affinity matrix comprising vinculin, SEQ ID NO: 7 or a fragment thereof can be bound to a solid support; the biological sample can be contacted to the affinity matrix to produce an affinity matrix-antibody complex (if the antibody is present); the affinity matrix-antibody complex can be separated from the remainder of the biological sample; and the antibody can be released from the affinity matrix. In another example, a label (e.g., fluorescent label) can be placed on vinculin, SEQ ID NO: 7 or a fragment thereof; the labeled vinculin, SEQ ID NO: 7 or a fragment thereof can be contacted with a biological sample to allow the antibody (if present) to bind specifically to the labeled vinculin, SEQ ID NO: 7 or a fragment thereof. In various embodiments, the labeled vinculin, SEQ ID NO: 7 or a fragment thereof can be separated out and analyzed for its binding to the antibody.

In various embodiments, CDT, CdtA, CdtB, CdtC, SEQ ID NOS: 1, 2, 4, 5 or a fragment thereof as discuss herein is used as a reagent (e.g., collector, trap) to bind anti-CDT antibodies (if present).

In certain embodiments, detecting the level an antibody that binds specifically to CDT, CdtA, CdtB, CdtC, SEQ ID NOS: 1, 2, 4, 5 or a fragment thereof as discuss herein or a fragment thereof may be performed by contacting CDT, CdtA, CdtB, CdtC, SEQ ID NOS: 1, 2, 4, 5 or a fragment thereof as discuss herein to a biological sample obtained from the subject to isolate the antibody that binds specifically to CDT, CdtA, CdtB, CdtC, SEQ ID NOS: 1, 2, 4, 5 or a fragment thereof as discuss herein.

In various embodiments, the fragment of CDT, CdtA, CdtB, CdtC, SEQ ID NOS: 1, 2, 4, 5 are those as described herein. As an example, an affinity matrix comprising CDT, CdtA, CdtB, CdtC, SEQ ID NOS: 1, 2, 4, 5 or a fragment thereof as discuss herein can be bound to a solid support; the biological sample can be contacted to the affinity matrix to produce an affinity matrix-antibody complex (if the antibody is present); the affinity matrix-antibody complex can be separated from the remainder of the biological sample; and the antibody can be released from the affinity matrix. In another example, a label (e.g., fluorescent label) can be placed on CDT, CdtA, CdtB, CdtC, SEQ ID NOS: 1, 2, 4, 5 or a fragment thereof as discuss herein or a fragment thereof; the labeled CDT, CdtA, CdtB, CdtC, SEQ ID NOS: 1, 2, 4, 5 or a fragment thereof as discuss herein can be contacted with a biological sample to allow the antibody (if present) to bind specifically to the labeled CDT, CdtA, CdtB, CdtC, SEQ ID NOS: 1, 2, 4, 5 or a fragment thereof as discuss herein. In various embodiments, the labeled CDT, CdtA, CdtB, CdtC, SEQ ID NOS: 1, 2, 4, 5 or a fragment thereof as discuss herein can be separated out and analyzed for its binding to the antibody.

In various embodiments, the assay comprises adding vinculin or a fragment thereof as discussed herein and CdtB or a fragment thereof as discussed herein to a biological sample from a subject desiring a determination regarding IBS, wherein anti-vinculin and/or anti-CdtB antibodies (if present in the biological sample) specifically binds to the vinculin or the fragment thereof and the CdtB or the fragment thereof in the biological sample; measuring the levels the anti-vinculin antibodies and the anti-CdtB antibodies in the biological sample; and identifying that the subject has IBS if the levels of the binding of the anti-vinculin antibodies is higher than the levels of the binding of the anti-CdtB antibodies.

Selecting Therapy Methods

Various embodiments of the present invention provide for a method of selecting a therapy for IBS, comprising: providing a biological sample from a subject desiring a diagnosis regarding IBS; assaying the biological sample for a level of anti-vinculin antibodies and a level of anti-CDT antibodies; determining the difference between the level of anti-vinculin antibodies and the level of anti-CDT antibodies; determining the presence of IBS when the level of anti-vinculin antibodies is higher than the level of anti-CDT antibodies; and selecting a therapy for IBS when the presence of IBS is determined.

Various embodiments of the present invention provide for a method of selecting a therapy for IBS: providing a biological sample from a subject desiring a diagnosis to distinguish between IBS and IBD; assaying the biological sample for a level of anti-vinculin antibodies and a level of anti-CDT antibodies; determining the difference between the level of anti-vinculin antibodies and the level of anti-CDT antibodies; determining the presence of IBS when the level of anti-vinculin antibodies is higher than the level of anti-CDT antibodies; and selecting a therapy for IBS when the presence of IBS is determined.

Assaying the biological samples can be performed as described herein.

In various embodiments, the subject is determined to have IBS if the level of anti-vinculin antibodies is 1, 2, 3, 4, 5, 6, 7, 8, 9, 10, 15, 20, 25, 30, 45, 50, 55, 60, 65, 70, 75, 80, 85, 90, 95, 100, 125, 150, 175, 200, 250, 300, 350, 400, 450, 500, 600, 700, 800, 900, or 1000% or more higher than the level of anti-CDT antibodies. In various embodiments, the extent of the level of anti-vinculin antibodies that is greater than anti-CDT antibodies provides a positive predictive value regarding the presence of IBS. The percentage in relation to the positive predictive value can be as described herein. In some embodiments, the percentage in relation to the positive predictive value can be calculated by examining additional IBS patients vs. controls or additional IBS patients vs. IBD patients for their levels of anti-vinculin antibodies and anti-CDT antibodies.

In certain embodiments, optical density (OD) is used to measure the level of anti-vinculin antibodies and anti-CDT antibodies. Thus, when the difference between the OD of anti-vinculin antibodies ($OD_V$) and OD of anti-CDT antibodies ($OD_{CDT}$) is greater than 0, the subject is determined to have IBS. In various embodiments, when $OD_V$–$OD_{CDT}$ is greater than 0.1, 0.2, 0.3, 0.4, 0.5, or 0.6, the subject is determined to have IBS. In certain embodiments, when $OD_V$–$OD_{CDT}$ is greater than 0.2, the subject is determined to have IBS. In various embodiments, the extent of $OD_V$–$OD_{CDT}$ provides a positive predictive value regarding the presence of IBS. The $OD_V$–$OD_{CDT}$ value in relation to the positive predictive value can be as described herein. In some embodiments, the $OD_V$–$OD_{CDT}$ value in relation to the positive predictive value can be calculated by examining additional IBS patients vs. controls or additional IBS patients vs. IBD patients for their levels of anti-vinculin antibodies and anti-CDT antibodies.

Selecting a therapy as used herein, includes but is not limited to selecting, choosing, prescribing, advising, recommending, instructing, or counseling the subject with respect to the treatment.

In various embodiments, the method further comprises administering the therapy to treat the IBS.

In various embodiments, the therapy selected or administered is a therapy as described herein. In various embodiments, the therapy selected or administered is an available therapy at the time of the present invention. In various embodiments, the available therapy comprises administering a course of antibiotic therapy to treat the IBS. In various embodiments, the therapy is an available IBS therapy in the prior art. In various embodiments, the available therapy is an experimental therapy for IBS, for example, a therapy that is undergoing FDA approval for the treatment of IBS.

In various embodiments, assaying the biological sample for a level of anti-vinculin antibodies and a level of anti-CDT antibodies can be performed as described herein.

In various embodiments, the subject can be a subject presenting one or more symptoms IBS; for example, constipation, diarrhea, bloating, abdominal pain.

In various embodiments, the IBS can be C-IBS, D-IBS, A-IBS (also known as M-IBS). In various embodiments, the IBS is severe IBS. In various embodiments, the IBS is severe C-IBS, severe-D-IBS, or severe A-IBS.

In various embodiments, the anti-CDT antibodies are anti-CdtB antibodies.

Examples of antibiotics include but are not limited to aminoglycosides (e.g., amikacin, gentamicin, kanamycin, neomycin, netilmicin, streptomycin, tobramycin, paromomycin), ansamycins (e.g., geldanamycin, herbimycin), carbacephems (e.g., loracarbef), carbapenems (e.g., ertapenem, doripenem, imipenem, cilastatin, meropenem), cephalosporins (e.g., first generation: cefadroxil, cefazolin, cefalotin or cefalothin, cefalexin; second generation: cefaclor, cefamandole, cefoxitin, cefprozil, cefuroxime; third generation: cefixime, cefdinir, cefditoren, cefoperazone, cefotaxime, cefpodoxime, ceftazidime, ceftibuten, ceftizoxime, ceftriaxone; fourth generation: cefepime; fifth generation: ceftobiprole), glycopeptides (e.g., teicoplanin, vancomycin), macrolides (e.g., azithromycin, clarithromycin, dirithromycin, erythromycin, roxithromycin, troleandomycin, telithromycin, spectinomycin), monobactams (e.g., aztreonam), penicillins (e.g., amoxicillin, ampicillin, azlocillin, carbenicillin, cloxacillin, dicloxacillin, flucloxacillin, mezlocillin, meticillin, nafcillin, oxacillin, penicillin, piperacillin, ticarcillin), antibiotic polypeptides (e.g., bacitracin, colistin, polymyxin b), quinolones (e.g., ciprofloxacin, enoxacin, gatifloxacin, levofloxacin, lomefloxacin, moxifloxacin, norfloxacin, ofloxacin, trovafloxacin), rifamycins (e.g., rifampicin or rifampin, rifabutin, rifapentine, rifaximin), sulfonamides (e.g., mafenide, prontosil, sulfacetamide, sulfamethizole, sulfanilamide, sulfasalazine, sulfisoxazole, trimethoprim, trimethoprim-sulfamethoxazole (co-trimoxazole, "tmp-smx"), and tetracyclines (e.g., demeclocycline, doxycycline, minocycline, oxytetracycline, tetracycline) as well as arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin combination, and tinidazole, or a combination thereof. In various embodiments, the antibiotics are a combination of rifaximin and neomycin. In various embodiments, the antibiotics are a combination of rifaximin and doxycycline. In various embodiments, the antibiotics are a combination of rifaximin and metronidazole.

In various embodiments, the antibiotics are non-absorbable antibiotics. Examples of non-absorbable antibiotics include but are not limited to rifaximin, neomycin, Bacitracin, vancomycin, teicoplanin, ramoplanin, and paromomycin.

Examples of additional IBS therapies include fiber supplements (e.g., METAMUCIL, CITRUCEL), osmotic laxatives (e.g., milk of magnesia, polyethylene glycol), anti-diarrheal medications (e.g., loperamide (IMODIUM), bile acid binders (e.g., cholestyramine (PREVALITE), colestipol (COLESTID) or colesevelam (WELCHOL), anticholinergic and antispasmodic medications (e.g., hyoscyamine (LEVSIN) and dicyclomine (BENTYL), antidepressant medications (e.g., tricyclic antidepressant (e.g., imipramine (TOFRANIL) or nortriptyline (PAMELOR)) or a selective serotonin reuptake inhibitor (SSRI) (e.g., fluoxetine (PROZAC, SARAFEM) or paroxetine (PAXIL)), Alosetron (LOTRONEX) and Lubiprostone (AMITIZA). Recent therapies for the treatment of constipation IBS include secretagogues such as lubiprostone (a chloride channel activator (AMITIZA)) and linaclotide (a guanylate cyclase C agonist (LINZESS)).

Dilution of Biological Samples and Antigens

In various embodiments, when determining the presence or level of anti-vinculin antibodies, the vinculin protein or a fragment thereof as described herein is used as the antigen at about 1.2 µg/ml concentration. In other embodiments, the concentration can be about 0.1, 0.2, 0.3, 0.4, 0.5, 0.6, 0.7, 0.8, 0.9, 1.0, 1.1, 1.3, 1.4, 1.5, 1.6, 1.7, 1.8, 1.9 or 2.0 µg/ml concentration.

In various embodiments, an about 1:16 dilution of the biological sample (e.g., plasma, serum) is used in the determination of the presence or level of anti-vinculin antibodies. In other embodiments, an about 1:8, 1:9, 1:10; 1:11, 1:12, 1:13, 1:14, 1:15, 1:16, 1:17; 1:18, 1:19, 1:20, 1:22, 1:24, 1:26, 1:28, 1:30, 1:32, 1:34, 1:36, 1:38, 1:40, 1:42, 1:44, 1:46, or 1:48 dilution of the biological sample (e.g., plasma, serum) is used in the determination of the presence or level of anti-vinculin antibodies. In other embodiments, an about 1:8 to 1:48 dilution of the biological sample (e.g., plasma, serum) is used in the determination of the presence or level of anti-vinculin antibodies.

In various embodiments, an about 1:32 dilution of the biological sample (e.g., plasma, serum) is used in the determination of the presence or level of anti-vinculin antibodies. In other embodiments, an about 1:8, 1:10, 1:12; 1:16, 1:20, 1:24, 1:30, 1:36, 1:48, or 1:64 dilution of the biological sample (e.g., plasma, serum) is used in the determination of the presence or level of anti-vinculin antibodies. In other embodiments, an about 1:8 to 1:64 dilution of the biological sample (e.g., plasma, serum) is used in the determination of the presence or level of anti-vinculin antibodies. In other embodiments, an about 1:5 to 1:10, 1:10-1:25, 1:25-1:50, 1:50-1:100, 1:100-1:200, 1:200-1:300, 1:300-1:400, 1:400-1:500, 1:500-1-600, or 1-600-1:100 dilution of the biological sample (e.g., plasma, serum) is used in the determination of the presence or level of anti-vinculin antibodies.

In various embodiments, when determining the presence or level of anti-CdtB antibodies, CdtB protein or a fragment thereof as described herein is used as the antigen at about 1.2 µg/ml concentration. In other embodiments, the concentration can be about 0.1, 0.2, 0.3, 0.4, 0.5, 0.6, 0.7, 0.8, 0.9, 1.0, 1.1, 1.3, 1.4, 1.5, 1.6, 1.7, 1.8, 1.9 or 2.0 µg/ml concentration.

In various embodiments, an about 1:16 dilution of the biological sample (e.g., plasma, serum) is used in the determination of the presence or level of anti-CdtB antibodies. In other embodiments, an about 1:8, 1:9, 1:10; 1:11, 1:12, 1:13, 1:14, 1:15, 1:16, 1:17; 1:18, 1:19, 1:20, 1:22, 1:24, 1:26, 1:28, 1:30, 1:32, 1:34, 1:36, 1:38, 1:40, 1:42, 1:44, 1:46, or 1:48 dilution of the biological sample (e.g., plasma, serum) is used in the determination of the presence or level of anti-CdtB antibodies. In other embodiments, an about 1:8 to 1:48 dilution of the biological sample (e.g., plasma, serum) is used in the determination of the presence or level of anti-CdtB antibodies.

In various embodiments, a 1:512 dilution of the biological sample (e.g., plasma, serum) is used in the determination of the presence or level of anti-CdtB antibodies. In other embodiments, an about 1:128, 1:256, 1:768, or 1:1024 dilution of the biological sample (e.g., plasma, serum) is used in the determination of the presence or level of anti-CdtB antibodies. In other embodiments, an about 1:100, 1:150, 1:200, 1:250, 1:300, 1:350, 1:400, 1:500, 1:550; 1:600, 1:650, 1:700, 1:750, 1:800, 1:850, 1:900, 1:950, or 1:1000 dilution of the biological sample (e.g., plasma, serum) is used in the determination of the presence or level of anti-CdtB antibodies. In other embodiments, an about 1:100-1:1000 dilution of the biological sample (e.g., plasma, serum) is used in the determination of the presence or level of anti-CdtB antibodies. In other embodiments, an about 1:5 to 1:10, 1:10-1:25, 1:25-1:50, 1:50-1:100, 1:100-1:200, 1:200-1-3:00, 1:300-1:400, 1:400-1:500, 1:500-1-600, or 1-600-1:100 dilution of the biological sample (e.g., plasma, serum) is used in the determination of the presence or level of anti-CdtB antibodies.

In various embodiments, if the dilution of the biological sample is different for the determination of the level of anti-vinculin antibodies and the level of anti-CdtB antibodies, and OD is used, then there will be an adjustment to the difference in OD.

Treatments

Various embodiments provide for methods for treating IBS.

In various embodiments, the method can comprise measuring for the presence of anti-vinculin antibodies that is greater than the presence of anti-CDT antibodies in a biological sample obtained from a subject; and administering an IBS therapy to the subject.

In various embodiments, the method can comprise providing a biological sample from a subject desiring a diagnosis regarding IBS; assaying the biological sample for a level of anti-vinculin antibodies and a level of anti-CDT antibodies; determining the difference between the level of anti-vinculin antibodies and the level of anti-CDT antibodies; determining the presence of IBS when the level of anti-vinculin antibodies is higher than the level of anti-CDT antibodies; and administering a therapy for IBS when the presence of IBS is determined.

In various embodiments, the method can comprise providing a biological sample from a subject desiring a diagnosis to distinguish between IBS and IBD; assaying the biological sample for a level of anti-vinculin antibodies and a level of anti-CDT antibodies; determining the difference between the level of anti-vinculin antibodies and the level of anti-CDT antibodies; determining the presence of IBS when the level of anti-vinculin antibodies is higher than the level of anti-CDT antibodies; and administering a therapy for IBS when the presence of IBS is determined.

Assaying the biological samples can be performed as described herein.

In various embodiments, the subject is determined to have IBS if the level of anti-vinculin antibodies is 1, 2, 3, 4, 5, 6, 7, 8, 9, 10, 15, 20, 25, 30, 45, 50, 55, 60, 65, 70, 75, 80, 85, 90, 95, 100, 125, 150, 175, 200, 250, 300, 350, 400, 450, 500, 600, 700, 800, 900, or 1000% or more higher than the level of anti-CDT antibodies. In various embodiments, the extent of the level of anti-vinculin antibodies that is greater than anti-CDT antibodies provides a positive predictive value regarding the presence of IBS. The percentage in relation to the positive predictive value can be as described herein. In some embodiments, the percentage in relation to the positive predictive value can be calculated by examining additional IBS patients vs. controls or additional IBS patients vs. IBD patients for their levels of anti-vinculin antibodies and anti-CDT antibodies.

In certain embodiments, optical density (OD) is used to measure the level of anti-vinculin antibodies and anti-CDT antibodies. Thus, when the difference between the OD of anti-vinculin antibodies ($OD_V$) and OD of anti-CDT antibodies ($OD_{CDT}$) is greater than 0, the subject is determined to have IBS. In various embodiments, when $OD_V$–$OD_{CDT}$ is greater than 0.1, 0.2, 0.3, 0.4, 0.5, or 0.6, the subject is determined to have IBS. In certain embodiments, when $OD_V$–$OD_{CDT}$ is greater than 0.2, the subject is determined to have IBS. In various embodiments, the extent of $OD_V$–$OD_{CDT}$ provides a positive predictive value regarding the presence of IBS. The $OD_V$–$OD_{CDT}$ value in relation to the positive predictive value can be as described herein. In some embodiments, the $OD_V$–$OD_{CDT}$ value in relation to the positive predictive value can be calculated by examining additional IBS patients vs. controls or additional IBS patients vs. IBD patients for their levels of anti-vinculin antibodies and anti-CDT antibodies.

In various embodiments, the therapy administered is a therapy as described herein. In various embodiments, the therapy administered is an available therapy at the time of the present invention. In various embodiments, the available therapy comprises administering a course of antibiotic therapy to treat the IBS. In various embodiments, the therapy is an available therapy in the prior art.

In various embodiments, assaying the biological sample for a level of anti-vinculin antibodies and a level of anti-CDT antibodies can be performed as described by the methods or systems of the present invention.

In various embodiments, the subject can be a subject presenting one or more symptoms IBS; for example, constipation, diarrhea, bloating, abdominal pain.

In various embodiments, the IBS can be C-IBS, D-IBS, A-IBS (also known as M-IBS). In various embodiments, the IBS is severe IBS. In various embodiments, the IBS is severe C-IBS, severe-D-IBS, or severe A-IBS.

In various embodiments, the anti-CDT antibodies are anti-CdtB antibodies.

In various embodiments, the method can comprise providing an anti-vinculin antibody neutralizing or inhibiting agent and administering the anti-vinculin antibody neutralizing or inhibiting agent to a subject in need thereof to neutralize or inhibit the anti-vinculin antibody.

In various embodiments, the anti-vinculin antibody neutralizing or inhibiting agent is a polypeptide capable of binding to the anti-vinculin antibody and neutralizing or inhibiting its function.

In various embodiments, the anti-vinculin antibody neutralizing or inhibiting agent is a polypeptide capable of binding to an antigen binding site of the anti-vinculin antibody. While not wishing to be bound by any particular theory, the inventors believe that these polypeptides can serves as a decoy to the anti-vinculin antibody. In various embodiments, the polypeptides are CDT pentapeptides as disclosed by Lucchese and Delfino (*Developing an anti-Campylobacter jejuni vaccine*. Immunopharmacology and Immunotoxicology, 2012; Early Online: 1-6), which is hereby incorporated by reference in its entirety as though fully set forth.

In various embodiments, the anti-vinculin antibody neutralizing or inhibiting agent is a small molecule capable of binding to the anti-vinculin antibody and neutralizing or inhibiting its function.

In various embodiments, the anti-vinculin antibody neutralizing or inhibiting agent is a small molecule capable of binding to an antigen binding site of the anti-vinculin antibody.

In various embodiments, the method can comprise providing an agent to change vinculin from an inactive state to an active state; and administering the agent to a subject in need thereof to treat the IBS.

In various embodiments, the agent to change vinculin from an inactive state to an active state is a small molecule capable of activating vinculin.

In various embodiments, the method can comprise providing a vinculin agonist; and administering the vinculin agonist to a subject in need thereof to treat the IBS. In certain embodiments, the vinculin agonist can be vinculin activating peptide (VAP) as disclosed by Nelson et al., *Vinculin Activators Target Integrins from Within the Cell to Increase Melanoma Sensitivity to Chemotherapy*, MOL CANCER RES JUNE 2011 9; 712 (published online Apr. 1, 2011), which is hereby incorporated by reference in its entirety as though fully set forth. In various embodiments, the VAP can be residues 500-633 of invasin protein IpaA of *Shigella*.

The protein sequence of IpaA of *Shigella*:

```
                                              (SEQ ID NO: 8)
MHNVNNTQAP TFLYKATSPS STEYSELKSK ISDIHSSQTS

LKTPASVSEK ENFATSFNQK CLDFLFSSSG KEDVLRSIYS

NSMNAYAKSE ILEFSNVLYS LVHQNGLNFE NEKGLQKIVA

QYSELIIKDK LSQDSAFGPW SAKNKKLHQL RQNIEHRLAL

LAQQHTSGEA LSLGQKLLNT EVSSFIKNNI LAELKLSNET

VSSLKLDDLV DAQAKLAFDS LRNQRKNTID SKGFGIGKLS

RDLNTVAVFP ELLRKVLNDI LEDIKDSHPI QDGLPTPPED

MPDGGPTPGA NEKTSQPVIH YHINNDNRTY DNRVFDNRVY

DNSYHENPEN DAQSPTSQTN DLLSRNGNSL LNPQRALVQK

VTSVLPHSIS DTVQTFANNS ALEKVFNHTP DNSDGIGSDL

LTTSSQERSA NNSLSRGHRP LNIQNSSTTP PLHPEGVTSS

NDNSSDTTKS SASLSHRVAS QINKFNSNTD SKVLQTDFLS

RNGDTYLTRE TIFEASKKVT NSLSNLISLI GTKSGTQERE

LQEKSKDITK STTEHRINNK LKVTDANIRN YVTETNADTI

DKNHAIYEKA KEVSSALSKV LSKIDDTSAE LLTDDISDLK

NNNDITAENN NIYKAAKDVT TSLSKVLKNI NKD
```

In various embodiments, the method can comprise providing a vinculin activator; and administering the vinculin activator to a subject in need thereof to treat the IBS. In certain embodiments, the vinculin activator can be talin, f-actin, a-catenin, or combinations thereof.

In various embodiments, the present invention provides pharmaceutical compositions including a pharmaceutically acceptable excipient along with a therapeutically effective amount of the agents described herein. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral. "Transdermal" administration may be accomplished using a topical cream or ointment or by means of a transdermal patch. Via the topical route, the pharmaceutical compositions based on compounds according to the invention may be formulated for treating the skin and mucous membranes and are in the form of ointments, creams, milks, salves, powders, impregnated pads, solutions, gels, sprays, lotions or suspensions. They can also be in the form of microspheres or nanospheres or lipid vesicles or polymer vesicles or polymer patches and hydrogels allowing controlled release. These topical-route compositions can be either in anhydrous form or in aqueous form depending on the clinical indication. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the parenteral route, the compositions may be in the form of solutions or suspensions for infusion or for injection.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins Pa., USA) (2000).

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1—Measurement of Anti-Vinculin and Anti-CD TB Antibodies

STEP 1—Antigen Immobilization: Each 96-well plate is coated overnight (>16 hours) at 4° C. in a humidified box with 100 µl/well of antigen (vinculin or CdtB) @ 1.2 µg/ml in BBS, approximate pH is 8.2. An additional well is coated, with each sample, with only BBS to determine non-specific background due to serum that will be subtracted from antigen coated well STEP 2—Wash #1—Wells were washed 3 times with approximately 250 µl/well of 0.05% PBS-T STEP 3—Block—Wells were blocked with 200 µl/well of 3% BSA in PBS for 1 hour at room temperature in a humidified box STEP 4—Prepare Serum & Dispense—Sera are diluted to a 1:16 dilution using 3% BSA in PBS. 100 µl/well of serum was added. Incubated for 1 hour at room temperature in humidified box.

STEP 5—Wash #2—Wells were washed 3 times with approximately 250 µl/well of 0.05% PBS-T STEP 6—Create Secondary Solution & Dispense—100 µl/well of a 1:10,000 secondary antibody conjugated to HRP diluted in 3% BSA in PBS as added. Incubated for 1 hr at room temperature in humidified box.

STEP 7—Wash #3—Wells were washed 6 times with approximately 250 μl/well of 0.05% PBS-T STEP 8—Detection—100 μl/well of TMB substrate solution (1-Step Ultra TMB—ELISA Substrate, Pierce, 34028) was added. Plate was immediately read on plate reader (BioTek Synergy HT) using an absorbance protocol at 370 nm; and was allowed to develop for 90 min (assay plateaued around 60 min.).

Example 2

Blood samples were taken from the following subjects and analyzed for the levels of anti-vinculin antibodies and anti-CDTB antibodies. Healthy subjects: 26 consecutive subjects who after filling out a questionnaire were found to have no bowel symptoms. IBD subjects: 30 subjects (15 CD and 15 UC). Active IBD proven by endoscopy with no immunomodulator therapy. IBS subjects: 162 subjects (100 from Beth Israel and 62 from Cedars-Sinai); Rome criteria positive. The results are shown in the tables below. PPV=Positive Predictive Value

TABLE 1

Difference between $OD_V$ and $OD_{CDTB}$

| $OD_V - OD_{CDT}$ threshold | Compared to healthy | | | Compared to IBD | | |
| --- | --- | --- | --- | --- | --- | --- |
| | Sensitivity | Specificity | PPV | Sensitivity | Specificity | PPV |
| >0.6 | 20 | 100 | 100 | 20 | 93 | 94 |
| >0.2 | 41 | 85 | 94 | 41 | 88 | 94 |
| >0.1 | 48 | 77 | 93 | 48 | 83 | 94 |
| >0 | 56 | 73 | 93 | 48 | 89 | 96 |

The results were further analyzed to control for IBD when using an assumption that 10% of IBD patients has IBS. The rate of positive antibody in IBS was taken and applied to the 10% of IBD patient (i.e., removed them from the analysis).

Table 2A and 2B. Controlling for IBS in IBD Patients.

TABLE 2A

| Vinculin | Compared to IBD | | |
| --- | --- | --- | --- |
| OD threshold | Sensitivity | Specificity | PPV |
| >1.0 | 30 | 85 | 92 |
| >0.8 | 59 | 70 | 92 |
| >0.5 | 59 | 70 | 92 |

TABLE 2B

| $OD_V - OD_{CDT}$ | Compared to IBD | | |
| --- | --- | --- | --- |
| threshold | Sensitivity | Specificity | PPV |
| >0.6 | 20 | 96 | 97 |
| >0.2 | 41 | 93 | 97 |
| >0.1 | 48 | 89 | 96 |
| >0 | 48 | 89 | 96 |

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method of detecting whether anti-vinculin antibodies are higher than anti-cytolethal distending toxin (CDT) antibodies, and optionally selecting a treatment for irritable bowel syndrome (IBS) or optionally administering an IBS therapy, comprising:
    assaying a biological sample obtained from a subject having a symptom of IBS and desiring a diagnosis regarding IBS or a diagnosis to distinguish IBS from inflammatory bowel syndrome (IBD) for a level of anti-vinculin antibodies and a level of anti-CDT antibodies; and
    determining the difference between the level of anti-vinculin antibodies and the level of anti-CDT antibodies.

2. The method of claim 1, wherein assaying the biological sample comprises:
    contacting vinculin or a 9-22 residue fragment thereof to the biological sample;
    contacting cytolethal distending toxin B (CdtB) or a 9-22 residue fragment thereof to the biological sample, wherein anti-vinculin and/or anti-CdtB antibodies specifically bind to the vinculin or the 9-22 residue fragment thereof and/or the CdtB or the 9-22 residue fragment thereof in the biological sample; and
    measuring the levels of the anti-vinculin antibodies and the anti-CdtB antibodies in the biological sample.

3. The method of claim 1, wherein determining the difference between the level of anti-vinculin antibodies and the level of anti-CDT antibodies comprises determining whether the level of anti-vinculin antibodies is 25% or more higher than the level of anti-CDT antibodies.

4. The method of claim 1, wherein optical density (OD) is used to measure the level of anti-vinculin antibodies and anti-CDT antibodies, and OD of anti-vinculin antibodies–OD of anti-CDT antibodies ($OD_V$–$OD_{CDT}$) is greater than 0 indicates that anti-vinculin antibodies are higher than anti-CDT antibodies.

5. The method of claim 4, wherein OD of anti-vinculin antibodies–OD of anti-CDT antibodies ($OD_V$–$OD_{CDT}$) is greater than 0.2 indicates that anti-vinculin antibodies are higher than anti-CDT antibodies.

6. The method of claim 1, wherein the anti-vinculin antibody is an antibody that binds specifically to vinculin.

7. The method of claim 1, wherein the anti-vinculin antibody is an antibody that binds specifically to a 9, 10, 11, 12, 13, 14, 15, 16, 17, 18, 19, 20, 21, or 22 residue peptide that has at least 95%, 96%, 97%, 98%, 99% or 100% homology with 9, 10, 11, 12, 13, 14, 15, 16, 17, 18, 19, 20, 21, or 22 contiguous residues of vinculin or SEQ ID NO.:7.

8. The method of claim 1, wherein the anti-vinculin antibody binds specifically to a polypeptide comprising 9, 10, 11, 12, 13, 14, 15, 16, 17, 18, 19, 20, 21, or 22 residues that has at least 95%, 96%, 97%, 98%, 99% or 100% homology with 9, 10, 11, 12, 13, 14, 15, 16, 17, 18, 19, 20, 21, or 22 contiguous residues of vinculin or SEQ ID NO:7.

9. The method of claim 1, wherein the anti-CDT antibody binds specifically to the cytolethal distending toxin B (CdtB) subunit of CDT.

10. The method of claim 9, wherein the CdtB amino acid sequence is *Campylobacter jejuni* cytolethal distending toxin B (SEQ ID NO: 5).

11. The method of claim 6, wherein the anti-CDT antibody binds specifically to an amino acid sequence at least 80%, 85%, 90%, 95%, 96%, 97%, 98%, or 99% identical to SEQ ID NO: 5.

12. The method of claim 9, wherein the CdtB amino acid sequence is *Campylobacter coli* cytolethal distending toxin B (SEQ ID NO: 1).

13. The method of claim 1, wherein the anti-CDT antibody binds specifically to an amino acid sequence at least 80%, 85%, 90%, 95%, 96%, 97%, 98%, or 99% identical to SEQ ID NO: 1.

14. The method of claim 1, wherein the anti-CDT antibody binds specifically to a polypeptide comprising 9, 10, 11, 12, 13, 14, 15, 16, 17, 18, 19, 20, 21, or 22 residues that has at least 95%, 96%, 97%, 98%, 99% or 100% homology with 9, 10, 11, 12, 13, 14, 15, 16, 17, 18, 19, 20, 21, or 22 contiguous residues of CdtB.

15. The method of claim 1, further comprising selecting an IBS treatment for the subject if the level of anti-vinculin antibodies is higher than the level of anti-CDT antibodies.

16. The method of claim 1, further comprising administering an IBS therapy to the subject if the level of anti-vinculin antibodies is higher than the level of anti-CDT antibodies.

17. A system, comprising:
an isolated biological sample from a subject desiring a diagnosis regarding IBS; and
one or more assays for detecting a level of anti-vinculin antibodies and a level of anti-cytolethal distending toxin (CDT) antibodies to diagnose IBS.

18. A system, comprising:
an isolated biological sample from a subject desiring a diagnosis to distinguish between IBS and IBD; and
one or more assays to detect a level of anti-vinculin antibodies and a level of anti-cytolethal distending toxin (CDT) antibodies to distinguish between IBS and IBD.

19. The system of claim 17, further comprising a machine for determining a presence of IBS when the level of anti-vinculin antibodies is higher than the level of anti-CDT antibodies.

20. The system of claim 19, further comprising an output or display element for displaying whether the patient has IBS, and/or for displaying whether the anti-vinculin antibodies is higher than the level of anti-CDT antibodies.

* * * * *

SEQUENCE LISTING

<160> NUMBER OF SEQ ID NOS: 8

<210> SEQ ID NO 1
<211> LENGTH: 267
<212> TYPE: PRT
<213> ORGANISM: Campylobacter coli

<400> SEQUENCE: 1

```
Met Lys Lys Ile Val Phe Leu Ile Leu Ser Phe Asn Val Leu Phe Ala
1               5                   10                  15

Ala Leu Glu Asn Tyr Asn Thr Gly Thr Trp Asn Leu Gln Gly Ser Ser
            20                  25                  30
```

```
Ala Ala Thr Glu Ser Lys Trp Asn Val Ser Ile Arg Gln Leu Ile Thr
             35                  40                  45
Gly Ala Asn Pro Met Asp Val Leu Ala Val Gln Glu Ala Gly Val Leu
 50                  55                  60
Pro Ser Thr Ala Met Met Thr Pro Arg Gln Val Gln Pro Val Gly Val
65                  70                  75                  80
Gly Ile Pro Ile His Glu Tyr Ile Trp Asn Leu Gly Ser Val Ser Arg
                 85                  90                  95
Pro Ser Ser Val Tyr Ile Tyr Tyr Ser Arg Val Asp Val Gly Ala Asn
                100                 105                 110
Arg Val Asn Leu Ala Ile Val Ser Arg Val Gln Ala Asp Glu Val Phe
                115                 120                 125
Val Leu Pro Pro Pro Thr Val Ala Ser Arg Pro Ile Ile Gly Ile Arg
130                 135                 140
Ile Gly Asn Asp Ala Phe Phe Asn Ile His Ala Leu Ala Ser Gly Gly
145                 150                 155                 160
Asn Asp Ala Gly Ala Ile Val Ala Ala Val Asp Met Phe Phe Arg Asn
                165                 170                 175
Arg Pro Asp Ile Asn Trp Met Ile Leu Gly Asp Phe Asn Arg Glu Ser
                180                 185                 190
Gly Ala Leu Val Thr Leu Leu Asp Pro Asp Leu Arg Ala Arg Thr Arg
                195                 200                 205
Val Val Val Pro Pro Ser Ser Thr Gln Thr Ser Gly Arg Thr Ile Asp
210                 215                 220
Tyr Ala Ile Thr Gly Asn Ser Asn Thr Ala Ala Leu Tyr Asn Pro Pro
225                 230                 235                 240
Pro Ile Val Ala Ile Leu Ala Leu Glu Gly Leu Arg Thr Phe Leu Ala
                245                 250                 255
Ser Asp His Phe Pro Val Asn Phe Arg Arg Pro
                260                 265

<210> SEQ ID NO 2
<211> LENGTH: 804
<212> TYPE: DNA
<213> ORGANISM: Campylobacter coli

<400> SEQUENCE: 2
atgaaaaaaa tagtattttt gattttaagt tttaatgtat tatttgccgc tttagaaaat       60
tacaacaccg gaacttggaa tttgcaaggc tcatcagctg caactgaaag caaatggaat      120
gttagtataa gacaactcat aaccggtgca aatcctatgg atgttttagc tgttcaagaa      180
gcgggggttt tacctagtac agctatgatg actcctagac aggtacaacc cgtgggcgtg      240
ggtattccta tacatgaata catatggaat ttaggctctg tatcaagacc tagctctgtt      300
tatatatatt attctagagt ggatgtagga gcaaatcgtg tgaatttagc tatcgttagc      360
agagtgcaag cggatgaagt ttttgtttta ccccctccaa cagttgcttc aagaccctat      420
ataggcatac gcataggcaa tgatgctttt ttcaatatac acgctctagc aagtggggga      480
aatgacgcag gagccattgt cgctgctgtg gatatgtttt ttagaaatag acctgatatt      540
aattggatga ttttaggcga ttttaataga gaatcaggcg ccttagtaac cttgctagat      600
cctgacttaa gagcacgcac tcgcgtagtt gttccgcctt cttctacgca aacaagtgga      660
agaacgattg attatgctat cactggaaat tccaacactg cagctttata caacccacca      720
ccgatagttg cgattttagc tttagaagga ttaagaacct ttttggcttc agatcatttt      780
```
cctgtaaatt ttagaagacc ttag                                           804

<210> SEQ ID NO 3
<211> LENGTH: 17
<212> TYPE: PRT
<213> ORGANISM: Campylobacter jejuni

<400> SEQUENCE: 3

Leu Asp Tyr Ala Ile Thr Gly Asn Ser Asn Arg Gln Gln Thr Tyr Thr
1               5                   10                  15

Pro

<210> SEQ ID NO 4
<211> LENGTH: 18
<212> TYPE: PRT
<213> ORGANISM: Campylobacter jejuni

<400> SEQUENCE: 4

Cys Leu Asp Tyr Ala Ile Thr Gly Asn Ser Asn Arg Gln Gln Thr Tyr
1               5                   10                  15

Thr Pro

<210> SEQ ID NO 5
<211> LENGTH: 265
<212> TYPE: PRT
<213> ORGANISM: Campylobacter jejuni

<400> SEQUENCE: 5

Met Lys Lys Ile Ile Cys Leu Phe Leu Ser Phe Asn Leu Ala Phe Ala
1               5                   10                  15

Asn Leu Glu Asn Phe Asn Val Gly Thr Trp Asn Leu Gln Gly Ser Ser
            20                  25                  30

Ala Ala Thr Glu Ser Lys Trp Ser Val Ser Val Arg Gln Leu Val Ser
        35                  40                  45

Gly Ala Asn Pro Leu Asp Ile Leu Met Ile Gln Glu Ala Gly Thr Leu
    50                  55                  60

Pro Arg Thr Ala Thr Pro Thr Gly Arg His Val Gln Gln Gly Gly Thr
65                  70                  75                  80

Pro Ile Asp Glu Tyr Glu Trp Asn Leu Gly Thr Leu Ser Arg Pro Asp
                85                  90                  95

Arg Val Phe Ile Tyr Tyr Ser Arg Val Asp Val Gly Ala Asn Arg Val
            100                 105                 110

Asn Leu Ala Ile Val Ser Arg Met Gln Ala Glu Glu Val Ile Val Leu
        115                 120                 125

Pro Pro Pro Thr Thr Val Ser Arg Pro Ile Ile Gly Ile Arg Asn Gly
    130                 135                 140

Asn Asp Ala Phe Phe Asn Ile His Ala Leu Ala Asn Gly Gly Thr Asp
145                 150                 155                 160

Val Gly Ala Ile Ile Thr Ala Val Asp Ala His Phe Ala Asn Met Pro
                165                 170                 175

Gln Val Asn Trp Met Ile Ala Gly Asp Phe Asn Arg Asp Pro Ser Thr
            180                 185                 190

Ile Thr Ser Thr Val Asp Arg Glu Leu Ala Asn Arg Ile Arg Val Val
        195                 200                 205

Phe Pro Thr Ser Ala Thr Gln Ala Ser Gly Gly Thr Leu Asp Tyr Ala
    210                 215                 220

Ile Thr Gly Asn Ser Asn Arg Gln Gln Thr Tyr Thr Pro Pro Leu Leu

```
                225                 230                 235                 240

Ala Ala Ile Leu Met Leu Ala Ser Leu Arg Ser His Ile Val Ser Asp
                245                 250                 255

His Phe Pro Val Asn Phe Arg Lys Phe
                260             265

<210> SEQ ID NO 6
<211> LENGTH: 51
<212> TYPE: DNA
<213> ORGANISM: Campylobacter jejuni

<400> SEQUENCE: 6
cttgattatg caattacagg aaattcaaat agacaacaaa cctatactcc a              51

<210> SEQ ID NO 7
<211> LENGTH: 1066
<212> TYPE: PRT
<213> ORGANISM: Homo sapiens

<400> SEQUENCE: 7

Met Pro Val Phe His Thr Arg Thr Ile Glu Ser Ile Leu Glu Pro Val
1               5                   10                  15

Ala Gln Gln Ile Ser His Leu Val Ile Met His Glu Gly Glu Val
                20                  25                  30

Asp Gly Lys Ala Ile Pro Asp Leu Thr Ala Pro Val Ala Ala Val Gln
            35                  40                  45

Ala Ala Val Ser Asn Leu Val Arg Val Gly Lys Glu Thr Val Gln Thr
        50                  55                  60

Thr Glu Asp Gln Ile Leu Lys Arg Asp Met Pro Pro Ala Phe Ile Lys
65                  70                  75                  80

Val Glu Asn Ala Cys Thr Lys Leu Val Gln Ala Ala Gln Met Leu Gln
                85                  90                  95

Ser Asp Pro Tyr Ser Val Pro Ala Arg Asp Tyr Leu Ile Asp Gly Ser
                100                 105                 110

Arg Gly Ile Leu Ser Gly Thr Ser Asp Leu Leu Leu Thr Phe Asp Glu
            115                 120                 125

Ala Glu Val Arg Lys Ile Ile Arg Val Cys Lys Gly Ile Leu Glu Tyr
        130                 135                 140

Leu Thr Val Ala Glu Val Val Glu Thr Met Glu Asp Leu Val Thr Tyr
145                 150                 155                 160

Thr Lys Asn Leu Gly Pro Gly Met Thr Lys Met Ala Lys Met Ile Asp
                165                 170                 175

Glu Arg Gln Gln Glu Leu Thr His Gln Glu His Arg Val Met Leu Val
                180                 185                 190

Asn Ser Met Asn Thr Val Lys Glu Leu Leu Pro Val Leu Ile Ser Ala
            195                 200                 205

Met Lys Ile Phe Val Thr Thr Lys Asn Ser Lys Asn Gln Gly Ile Glu
        210                 215                 220

Glu Ala Leu Lys Asn Arg Asn Phe Thr Val Glu Lys Met Ser Ala Glu
225                 230                 235                 240

Ile Asn Glu Ile Ile Arg Val Leu Gln Leu Thr Ser Trp Asp Glu Asp
                245                 250                 255

Ala Trp Ala Ser Lys Asp Thr Glu Ala Met Lys Arg Ala Leu Ala Ser
                260                 265                 270

Ile Asp Ser Lys Leu Asn Gln Ala Lys Gly Trp Leu Arg Asp Pro Ser
            275                 280                 285
```

```
Ala Ser Pro Gly Asp Ala Gly Glu Gln Ala Ile Arg Gln Ile Leu Asp
    290                 295                 300
Glu Ala Gly Lys Val Gly Glu Leu Cys Ala Gly Lys Glu Arg Arg Glu
305                 310                 315                 320
Ile Leu Gly Thr Cys Lys Met Leu Gly Gln Met Thr Asp Gln Val Ala
                325                 330                 335
Asp Leu Arg Ala Arg Gly Gln Gly Ser Ser Pro Val Ala Met Gln Lys
            340                 345                 350
Ala Gln Gln Val Ser Gln Gly Leu Asp Val Leu Thr Ala Lys Val Glu
        355                 360                 365
Asn Ala Ala Arg Lys Leu Glu Ala Met Thr Asn Ser Lys Gln Ser Ile
    370                 375                 380
Ala Lys Lys Ile Asp Ala Ala Gln Asn Trp Leu Ala Asp Pro Asn Gly
385                 390                 395                 400
Gly Pro Glu Gly Glu Glu Gln Ile Arg Gly Ala Leu Ala Glu Ala Arg
                405                 410                 415
Lys Ile Ala Glu Leu Cys Asp Asp Pro Lys Glu Arg Asp Asp Ile Leu
            420                 425                 430
Arg Ser Leu Gly Glu Ile Ser Ala Leu Thr Ser Lys Leu Ala Asp Leu
        435                 440                 445
Arg Arg Gln Gly Lys Gly Asp Ser Pro Glu Ala Arg Ala Leu Ala Lys
    450                 455                 460
Gln Val Ala Thr Ala Leu Gln Asn Leu Gln Thr Lys Thr Asn Arg Ala
465                 470                 475                 480
Val Ala Asn Ser Arg Pro Ala Lys Ala Ala Val His Leu Glu Gly Lys
                485                 490                 495
Ile Glu Gln Ala Gln Arg Trp Ile Asp Asn Pro Thr Val Asp Asp Arg
            500                 505                 510
Gly Val Gly Gln Ala Ala Ile Arg Gly Leu Val Ala Glu Gly His Arg
        515                 520                 525
Leu Ala Asn Val Met Met Gly Pro Tyr Arg Gln Asp Leu Leu Ala Lys
    530                 535                 540
Cys Asp Arg Val Asp Gln Leu Thr Ala Gln Leu Ala Asp Leu Ala Ala
545                 550                 555                 560
Arg Gly Glu Gly Glu Ser Pro Gln Ala Arg Ala Leu Ala Ser Gln Leu
                565                 570                 575
Gln Asp Ser Leu Lys Asp Leu Lys Ala Arg Met Gln Glu Ala Met Thr
            580                 585                 590
Gln Glu Val Ser Asp Val Phe Ser Asp Thr Thr Pro Ile Lys Leu
        595                 600                 605
Leu Ala Val Ala Ala Thr Ala Pro Pro Asp Ala Pro Asn Arg Glu Glu
    610                 615                 620
Val Phe Asp Glu Arg Ala Ala Asn Phe Glu Asn His Ser Gly Lys Leu
625                 630                 635                 640
Gly Ala Thr Ala Glu Lys Ala Ala Ala Val Gly Thr Ala Asn Lys Ser
                645                 650                 655
Thr Val Glu Gly Ile Gln Ala Ser Val Lys Thr Ala Arg Glu Leu Thr
            660                 665                 670
Pro Gln Val Val Ser Ala Ala Arg Ile Leu Leu Arg Asn Pro Gly Asn
        675                 680                 685
Gln Ala Ala Tyr Glu His Phe Glu Thr Met Lys Asn Gln Trp Ile Asp
    690                 695                 700
```

```
Asn Val Glu Lys Met Thr Gly Leu Val Asp Glu Ala Ile Asp Thr Lys
705                 710                 715                 720

Ser Leu Leu Asp Ala Ser Glu Glu Ala Ile Lys Lys Asp Leu Asp Lys
            725                 730                 735

Cys Lys Val Ala Met Ala Asn Ile Gln Pro Gln Met Leu Val Ala Gly
                740                 745                 750

Ala Thr Ser Ile Ala Arg Arg Ala Asn Arg Ile Leu Leu Val Ala Lys
            755                 760                 765

Arg Glu Val Glu Asn Ser Glu Asp Pro Lys Phe Arg Glu Ala Val Lys
770                 775                 780

Ala Ala Ser Asp Glu Leu Ser Lys Thr Ile Ser Pro Met Val Met Asp
785                 790                 795                 800

Ala Lys Ala Val Ala Gly Asn Ile Ser Asp Pro Gly Leu Gln Lys Ser
                805                 810                 815

Phe Leu Asp Ser Gly Tyr Arg Ile Leu Gly Ala Val Ala Lys Val Arg
                820                 825                 830

Glu Ala Phe Gln Pro Gln Glu Pro Asp Phe Pro Pro Pro Pro Asp
                835                 840                 845

Leu Glu Gln Leu Arg Leu Thr Asp Glu Leu Ala Pro Pro Lys Pro Pro
850                 855                 860

Leu Pro Glu Gly Glu Val Pro Pro Arg Pro Pro Pro Glu Glu
865                 870                 875                 880

Lys Asp Glu Glu Phe Pro Glu Gln Lys Ala Gly Glu Val Ile Asn Gln
                885                 890                 895

Pro Met Met Met Ala Arg Gln Leu His Asp Glu Ala Arg Lys Trp
                900                 905                 910

Ser Ser Lys Gly Asn Asp Ile Ile Ala Ala Lys Arg Met Ala Leu
            915                 920                 925

Leu Met Ala Glu Met Ser Arg Leu Val Arg Gly Gly Ser Gly Thr Lys
930                 935                 940

Arg Ala Leu Ile Gln Cys Ala Lys Asp Ile Ala Lys Ala Ser Asp Glu
945                 950                 955                 960

Val Thr Arg Leu Ala Lys Glu Val Ala Lys Gln Cys Thr Asp Lys Arg
                965                 970                 975

Ile Arg Thr Asn Leu Leu Gln Val Cys Glu Arg Ile Pro Thr Ile Ser
                980                 985                 990

Thr Gln Leu Lys Ile Leu Ser Thr Val Lys Ala Thr Met Leu Gly Arg
                995                 1000                1005

Thr Asn Ile Ser Asp Glu Glu Ser Glu Gln Ala Thr Glu Met Leu
    1010                1015                1020

Val His Asn Ala Gln Asn Leu Met Gln Ser Val Lys Glu Thr Val
    1025                1030                1035

Arg Glu Ala Glu Ala Ala Ser Ile Lys Ile Arg Thr Asp Ala Gly
    1040                1045                1050

Phe Thr Leu Arg Trp Val Arg Lys Thr Pro Trp Tyr Gln
    1055                1060                1065

<210> SEQ ID NO 8
<211> LENGTH: 633
<212> TYPE: PRT
<213> ORGANISM: Shigella

<400> SEQUENCE: 8

Met His Asn Val Asn Asn Thr Gln Ala Pro Thr Phe Leu Tyr Lys Ala
1               5                   10                  15
```

```
Thr Ser Pro Ser Ser Thr Glu Tyr Ser Glu Leu Lys Ser Lys Ile Ser
            20                  25                  30

Asp Ile His Ser Ser Gln Thr Ser Leu Lys Thr Pro Ala Ser Val Ser
        35                  40                  45

Glu Lys Glu Asn Phe Ala Thr Ser Phe Asn Gln Lys Cys Leu Asp Phe
50                  55                  60

Leu Phe Ser Ser Gly Lys Glu Asp Val Leu Arg Ser Ile Tyr Ser
65                  70                  75                  80

Asn Ser Met Asn Ala Tyr Ala Lys Ser Glu Ile Leu Glu Phe Ser Asn
                85                  90                  95

Val Leu Tyr Ser Leu Val His Gln Asn Gly Leu Asn Phe Glu Asn Glu
                100                 105                 110

Lys Gly Leu Gln Lys Ile Val Ala Gln Tyr Ser Glu Leu Ile Ile Lys
            115                 120                 125

Asp Lys Leu Ser Gln Asp Ser Ala Phe Gly Pro Trp Ser Ala Lys Asn
    130                 135                 140

Lys Lys Leu His Gln Leu Arg Gln Asn Ile Glu His Arg Leu Ala Leu
145                 150                 155                 160

Leu Ala Gln Gln His Thr Ser Gly Glu Ala Leu Ser Leu Gly Gln Lys
                165                 170                 175

Leu Leu Asn Thr Glu Val Ser Ser Phe Ile Lys Asn Asn Ile Leu Ala
            180                 185                 190

Glu Leu Lys Leu Ser Asn Glu Thr Val Ser Ser Leu Lys Leu Asp Asp
        195                 200                 205

Leu Val Asp Ala Gln Ala Lys Leu Ala Phe Asp Ser Leu Arg Asn Gln
    210                 215                 220

Arg Lys Asn Thr Ile Asp Ser Lys Gly Phe Gly Ile Gly Lys Leu Ser
225                 230                 235                 240

Arg Asp Leu Asn Thr Val Ala Val Phe Pro Glu Leu Leu Arg Lys Val
                245                 250                 255

Leu Asn Asp Ile Leu Glu Asp Ile Lys Asp Ser His Pro Ile Gln Asp
            260                 265                 270

Gly Leu Pro Thr Pro Pro Glu Asp Met Pro Asp Gly Gly Pro Thr Pro
        275                 280                 285

Gly Ala Asn Glu Lys Thr Ser Gln Pro Val Ile His Tyr His Ile Asn
    290                 295                 300

Asn Asp Asn Arg Thr Tyr Asp Asn Arg Val Phe Asp Asn Arg Val Tyr
305                 310                 315                 320

Asp Asn Ser Tyr His Glu Asn Pro Glu Asn Asp Ala Gln Ser Pro Thr
                325                 330                 335

Ser Gln Thr Asn Asp Leu Leu Ser Arg Asn Gly Asn Ser Leu Leu Asn
            340                 345                 350

Pro Gln Arg Ala Leu Val Gln Lys Val Thr Ser Val Leu Pro His Ser
        355                 360                 365

Ile Ser Asp Thr Val Gln Thr Phe Ala Asn Asn Ser Ala Leu Glu Lys
    370                 375                 380

Val Phe Asn His Thr Pro Asp Asn Ser Asp Gly Ile Gly Ser Asp Leu
385                 390                 395                 400

Leu Thr Thr Ser Ser Gln Glu Arg Ser Ala Asn Asn Ser Leu Ser Arg
                405                 410                 415

Gly His Arg Pro Leu Asn Ile Gln Asn Ser Ser Thr Pro Pro Leu
            420                 425                 430
```

-continued

```
His Pro Glu Gly Val Thr Ser Ser Asn Asp Asn Ser Ser Asp Thr Thr
        435                 440                 445

Lys Ser Ser Ala Ser Leu Ser His Arg Val Ala Ser Gln Ile Asn Lys
    450                 455                 460

Phe Asn Ser Asn Thr Asp Ser Lys Val Leu Gln Thr Asp Phe Leu Ser
465                 470                 475                 480

Arg Asn Gly Asp Thr Tyr Leu Thr Arg Glu Thr Ile Phe Glu Ala Ser
                485                 490                 495

Lys Lys Val Thr Asn Ser Leu Ser Asn Leu Ile Ser Leu Ile Gly Thr
            500                 505                 510

Lys Ser Gly Thr Gln Glu Arg Glu Leu Gln Glu Lys Ser Lys Asp Ile
        515                 520                 525

Thr Lys Ser Thr Thr Glu His Arg Ile Asn Asn Lys Leu Lys Val Thr
    530                 535                 540

Asp Ala Asn Ile Arg Asn Tyr Val Thr Glu Thr Asn Ala Asp Thr Ile
545                 550                 555                 560

Asp Lys Asn His Ala Ile Tyr Glu Lys Ala Lys Glu Val Ser Ser Ala
                565                 570                 575

Leu Ser Lys Val Leu Ser Lys Ile Asp Asp Thr Ser Ala Glu Leu Leu
            580                 585                 590

Thr Asp Asp Ile Ser Asp Leu Lys Asn Asn Asn Asp Ile Thr Ala Glu
        595                 600                 605

Asn Asn Asn Ile Tyr Lys Ala Ala Lys Asp Val Thr Thr Ser Leu Ser
    610                 615                 620

Lys Val Leu Lys Asn Ile Asn Lys Asp
625                 630
```